United States Patent
Lu et al.

(10) Patent No.: US 11,976,288 B2
(45) Date of Patent: May 7, 2024

(54) ABIOTIC STRESS TOLERANT PLANTS AND METHODS

(71) Applicants: PIONEER OVERSEAS CORPORATION, Johnston, IA (US); SINOBIOWAY BIO-AGRICULTURE GROUP CO. LTD., Beijing (CN)

(72) Inventors: Guihua Lu, San Diego, CA (US); Guokui Wang, Beijing (CN); Guanfan Mao, Beijing (CN); Rongrong Jiao, Beijing (CN); Yu Zhang, Beijing (CN); Changgui Wang, Beijing (CN); Jiantao Wang, Beijing (CN); Yang Gao, Beijing (CN)

(73) Assignees: PIONEER OVERSEAS CORPORATION; SINOBIOWAY BIO-AGRICULTURE GROUP CO. LTD.

( * ) Notice: Subject to any disclaimer, the term of this patent is extended or adjusted under 35 U.S.C. 154(b) by 93 days.

(21) Appl. No.: 17/595,442

(22) PCT Filed: May 29, 2019

(86) PCT No.: PCT/CN2019/088990
§ 371 (c)(1),
(2) Date: Nov. 17, 2021

(87) PCT Pub. No.: WO2020/237524
PCT Pub. Date: Dec. 3, 2020

(65) Prior Publication Data
US 2022/0220496 A1 Jul. 14, 2022

(51) Int. Cl.
*C12N 15/82* (2006.01)
*C12N 9/22* (2006.01)

(52) U.S. Cl.
CPC ........... *C12N 15/8273* (2013.01); *C12N 9/22* (2013.01); *C12N 15/8213* (2013.01); *C12N 15/8218* (2013.01)

(58) Field of Classification Search
None
See application file for complete search history.

(56) References Cited

U.S. PATENT DOCUMENTS

2004/0123343 A1* 6/2004 La Rosa .............. C07K 14/415
                                                              800/278
2021/0071188 A1* 3/2021 Adams ............... C12N 15/8261

OTHER PUBLICATIONS

Guo et al, 2004, Protein tolerance to random amino acid change, Proceedings of the National Academy of Sciences, 101:9205-9210 (Year: 2004) (Year: 2014).*
NCBI, ABA94127.1, 2011, www.ncbi.nlm.nih.gov/protein/ABA94127.1?report=genbank&log$=prottop&blast_rank=1&RID=C4PN753A016 (Year: 2011).*
Uniprot, A0A0D3HMR1_9ORYZ, 2015, www.uniprot.org/uniprotkb/A0A0D3HMR1/entry (Year: 2015).*
Sasaki, T., et al. "hypothetical protein [*Oryza sativa Japonica* Group]" GenBank: BAD81141.1, Feb. 16, 2008.
International Search Report and Written Opinion for PCT/CN2019/088990, dated Mar. 2, 2020.

* cited by examiner

*Primary Examiner* — Anne Kubelik
*Assistant Examiner* — Aleksandar Radosavljevic

(57) ABSTRACT

Isolated polynucleotides and polypeptides, and recombinant DNA constructs are useful for conferring improved nitrogen stress tolerance or NUE and yield. Compositions (such as plants or seeds) comprise these recombinant DNA constructs; and methods utilize these recombinant DNA constructs. The recombinant DNA constructs comprise a polynucleotide operably linked to a promoter that is functional in a plant, wherein said polynucleotides encode nitrogen stress tolerance polypeptides.

12 Claims, No Drawings
Specification includes a Sequence Listing.

ABIOTIC STRESS TOLERANT PLANTS AND METHODS

FIELD

The field of the disclosure relates to plant breeding and genetics and, particularly, relates to improving tolerance to abiotic stress in plants.

REFERENCE TO SEQUENCE LISTING SUBMITTED ELECTRONICALLY

The official copy of the sequence listing is submitted electronically via EFS-Web as an ASCII formatted sequence listing with a file named RTS22593P_SeqListing.txt created on Oct. 26, 2021 and having a size of 100 kilobytes and is filed concurrently with the specification. The sequence listing comprised in this ASCII formatted document is part of the specification and is herein incorporated by reference in its entirety.

BACKGROUND

Stresses to plants may be caused by both biotic and abiotic agents. For example, biotic causes of stress include infection with pathogen, insect feeding, and parasitism by another plant such as mistletoe. Abiotic stresses include, for example, excessive or insufficient available water, temperature extremes, and synthetic chemicals such as herbicides.

Abiotic stress is the primary cause of crop loss worldwide, causing average yield losses more than 50% for major crops (Boyer, J. S. (1982) Science 218:443-448; Bray, E. A. et al. (2000) In Biochemistry and Molecular Biology of Plants, edited by Buchannan, B. B. et al., Amer. Soc. Plant Biol., pp. 1158-1249).

Accordingly, there is a need to develop compositions and methods that increase tolerance to abiotic stress in plants. This invention provides such compositions and methods.

SUMMARY

The following embodiments are among those encompassed by the disclosure:

In one embodiment, the present disclosure includes an isolated polynucleotide, encoding a polypeptide with amino acid sequence of at least 90% sequence identity to SEQ ID NO: 3, 6, 9, 12, 15, 18, 21 or 24, wherein increased expression of the polynucleotide in a plant enhances nitrogen stress tolerance or improves nitrogen use efficiency (NUE). In certain embodiments, the isolated polynucleotide encodes the amino acid sequence of SEQ ID NO: 3, 6, 9, 12, 15, 18, 21 or 24. In certain embodiments, the isolated polynucleotide comprises the nucleotide sequence of SEQ ID NO: 1, 2, 4, 5, 7, 8, 10, 11, 13, 14, 16, 17, 19, 20, 22 or 23. In certain embodiments, increased expression of the polynucleotide in a plant enhances grain yield under low nitrogen conditions and/or normal nitrogen conditions.

The present disclosure also provides a recombinant DNA construct comprising an isolated polynucleotide operably linked to at least one heterologous regulatory element, wherein the polynucleotide encodes a polypeptide with amino acid sequence of at least 90% sequence identity to SEQ ID NO: 3, 6, 9, 12, 15, 18, 21 or 24.

The present disclosure further provides a modified plant or seed having increased expression or activity of at least one polynucleotide encoding a polypeptide with amino acid sequence of at least 90% sequence identity to SEQ ID NO: 3, 6, 9, 12, 15, 18, 21 or 24. In certain embodiments, the modified plant or seed comprises in its genome a recombinant DNA construct comprising a polynucleotide operably linked to at least one heterologous regulatory element, wherein the polynucleotide encodes a polypeptide with amino acid sequence of at least 90% sequence identity to SEQ ID NO: 3, 6, 9, 12, 15, 18, 21 or 24. In certain embodiments, the modified plant exhibits improved nitrogen stress tolerance, NUE, and/or increased grain yield when grown under low nitrogen conditions and/or normal nitrogen conditions compared to a control plant.

In certain embodiments, the modified plant or seed comprises a targeted genetic modification at a genomic locus comprising a polynucleotide encoding a polypeptide with amino acid sequence of at least 90% sequence identity to SEQ ID NO: 3, 6, 9, 12, 15, 18, 21 or 24, wherein the targeted genetic modification increase the expression and/or activity of the polypeptide. In certain embodiments, the modified plant exhibits improved nitrogen stress tolerance, NUE, and/or increased grain yield when grown under low nitrogen conditions and/or normal nitrogen conditions compared to a control plant.

In certain embodiments, the plant is selected from the group consisting of rice, maize, soybean, sunflower, sorghum, canola, wheat, alfalfa, cotton, barley, millet, sugar cane and switchgrass.

Also provided are methods for increasing nitrogen stress tolerance or NUE in a plant, the method comprising increasing the expression of at least one polynucleotide encoding a polypeptide with amino acid sequence of at least 90% sequence identity to SEQ ID NO: 3, 6, 9, 12, 15, 18, 21 or 24. Wherein the obtained plant exhibits increased nitrogen stress tolerance or NUE when compared to the control plant.

In certain embodiments, the method for increasing nitrogen stress tolerance or NUE comprises: (a) introducing into a regenerable plant cell a recombinant DNA construct comprising a polynucleotide operably linked to at least one heterologous regulatory element, wherein the polynucleotide encodes a polypeptide having an amino acid sequence of at least 80% sequence identity, when compared to SEQ ID NO: 3, 6, 9, 12, 15, 18, 21 or 24; and (b) generating the plant, wherein the plant comprises in its genome the recombinant DNA construct.

In certain embodiments, the method for increasing nitrogen stress tolerance or NUE comprises: (a) introducing into a regenerable plant cell a targeted genetic modification at a genomic locus comprising a polynucleotide encoding a polypeptide having an amino acid sequence of at least 80% sequence identity, when compared to SEQ ID NO: 3, 6, 9, 12, 15, 18, 21 or 24; and (b) generating the plant, wherein the plant comprises in its genome the introduced genetic modification and has increased expression and/or activity of the polypeptide. In certain embodiments, the targeted genetic modification is introduced using a genome modification technique selected from the group consisting of a polynucleotide-guided endonuclease, CRISPR-Cas endonucleases, base editing deaminases, a zinc finger nuclease, a transcription activator-like effector nuclease (TALEN), an engineered site-specific meganucleases, or an Argonaute. In certain embodiments, the targeted genetic modification is present in (a) the coding region; (b) a non-coding region; (c) a regulatory sequence; (d) an untranslated region; or (e) any combination of (a)-(d) of the genomic locus that encodes a polypeptide comprising an amino acid sequence that is at 80% sequence identity, when compared to SEQ ID NO: 3, 6, 9, 12, 15, 18, 21 or 24.

BRIEF DESCRIPTION OF THE DRAWINGS AND SEQUENCE LISTING

The disclosure can be more fully understood from the following detailed description and the accompanying Sequence Listing which form a part of this application. The sequence descriptions and sequence listing attached hereto comply with the rules governing nucleotide and amino acid sequence disclosures in patent applications as set forth in 37 C.F.R. §§ 1.821 and 1.825. The sequence descriptions comprise the three letter codes for amino acids as defined in 37 C.F.R. §§ 1.821 and 1.825, which are incorporated herein by reference.

TABLE 1

Sequence Listing Description

| Source species | Clone Designation | SEQ ID NO: (Nucleotide) | SEQ ID NO: (Amino Acid) |
|---|---|---|---|
| Oryza sativa | OsLNTP12 | 1, 2 | 3 |
| Oryza sativa | OsLNTP13 | 4, 5 | 6 |
| Oryza sativa | OsGRRP1 | 7, 8 | 9 |
| Oryza sativa | OsLNTP14 | 10, 11 | 12 |
| Oryza sativa | OsLNTP15 | 13, 14 | 15 |
| Oryza sativa | OsLNTP16 | 16, 17 | 18 |
| Oryza sativa | OsLNTP17 | 19, 20 | 21 |
| Oryza sativa | OsPTR11 | 22, 23 | 24 |
| Artificial | Primers | 25-46 | n/a |
| Oryza sativa | LNTP12 paralog | 47 | 48 |
| Oryza sativa | LNTP13 paralog | 49 | 50 |
| Zea mays | GRRP1 homolog | 51 | 52 |
| Oryza sativa | LNTP14 paralog | 53 | 54 |
| Zea mays | LNTP14 homolog | 55 | 56 |
| Oryza sativa | LNTP15 paralog | 57 | 58 |
| Oryza sativa | PTR11 paralog | 59 | 60 |
| Zea mays | PTR11 homolog | 61 | 62 |

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

Definitions

As used herein, "increased nitrogen stress tolerance" of a plant refers to any measurable improvement in a physiological or physical characteristic, such as yield, as measured relative to a reference or control plant, when grown under low nitrogen and/or nitrogen limiting conditions. Typically, when a plant comprising a recombinant DNA construct or DNA modification in its genome exhibits increased nitrogen stress tolerance or NUE relative to a reference or control plant, the reference or control plant does not comprise in its genome the recombinant DNA construct or DNA modification.

As used herein "nitrogen use efficiency (NUE)" refers to the ratio between the amount of fertilizer N removed by a plant and the amount of fertilizer N applied. Accordingly, in certain embodiments an increase in N use efficiency refers to any detectable increase in the ratio between the amount of fertilizer N removed by a plant and the amount of fertilizer N applied. A person of ordinary skill in the art can calculate N use efficiency using routine methods in the art.

"Increased chlorate sensitivity" of a plant is measured relative to a reference or control plant and reflects ability of the plant to survive with less damage than a reference or control plant after treated with chlorate solution. In general, chlorate sensitivity can be used as a marker of abiotic stress tolerance, such as NUE.

"Agronomic characteristic" is a measurable parameter including but not limited to: greenness, grain yield, growth rate, total biomass or rate of accumulation, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control", "control plant" or "control plant cell" or the like provides a reference point for measuring changes in phenotype of a subject plant or plant cell in which genetic alteration, such as transformation, has been affected as to a gene of interest. For example, a control plant may be a plant having the same genetic background as the subject plant except for the genetic alteration that resulted in the subject plant or cell.

"Plant" includes reference to whole plants, plant organs, plant tissues, seeds and plant cells and progeny of the same. Plant cells include, without limitation, cells from seeds, suspension cultures, embryos, meristematic regions, callus tissues, leaves, roots, shoots, gametophytes, sporophytes, pollen, and microspores.

"Progeny" comprises any subsequent generation of a plant.

"Modified plant" includes reference to a plant which comprises within its genome a heterologous polynucleotide or modified gene or promoter. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", and "nucleic acid fragment" are used interchangeably and refer to a polymer of RNA or DNA that is single- or double-stranded, optionally containing synthetic, non-natural or altered nucleotide bases. Nucleotides (usually found in their 5'-monophosphate form) are referred to by their single-letter designation as follows: "A" for adenylate or deoxyadenylate, "C" for cytidylate or deoxycytidylate, and "G" for guanylate or deoxyguanylate for RNA or DNA, respectively; "U" for uridylate; "T" for deoxythymidylate; "R" for purines (A or G); "Y" for pyrimidines (C or T); "K" for G or T; "H" for A or C or T; "I" for inosine; and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, and sulfation, gamma-carboxylation of glutamic acid residues, hydroxylation and ADP-ribosylation.

"Recombinant DNA construct" refers to a combination of nucleic acid fragments that are not normally found together in nature. Accordingly, a recombinant DNA construct may comprise regulatory elements and coding sequences that are derived from different sources, or regulatory elements and coding sequences derived from the same source, but arranged in a manner different than that normally found in nature.

"Regulatory elements" refer to nucleotide sequences located upstream (5' non-coding sequences), within, or downstream (3' non-coding sequences) of a coding sequence, and influencing the transcription, RNA processing or stability, or translation of the associated coding sequence. Regulatory elements may include, but are not limited to, promoters, translation leader sequences, introns, and polyadenylation recognition sequences. The terms "regulatory sequence" and "regulatory element" and "regulatory region" are used interchangeably herein.

"Promoter" refers to a nucleic acid fragment capable of controlling transcription of another nucleic acid fragment. "Promoter functional in a plant" is a promoter capable of controlling transcription of genes in plant cells whether its origin is from a plant cell or not. "Tissue-specific promoter" and "tissue-preferred promoter" refers to a promoter that is expressed predominantly but not necessarily exclusively in one tissue or organ, but that may also be expressed in one specific cell or cell type. "Developmentally regulated promoter" is a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

As used herein "increased", "increase", or the like refers to any detectable increase in an experimental group (e.g., plant with a DNA modification described herein) as compared to a control group (e.g., wild-type plant that does not comprise the DNA modification). Accordingly, increased expression of a protein comprises any detectable increase in the total level of the protein in a sample and can be determined using routine methods in the art such as, for example, Western blotting and ELISA.

As used herein, "yield" refers to the amount of agricultural production harvested per unit of land, and may include reference to bushels per acre or kilograms per mu of a crop at harvest, as adjusted for grain moisture (e.g., typically 15% for maize, 13.5% for rice). Grain moisture is measured in the grain at harvest. The adjusted test weight of grain is determined to be the weight in pounds per bushel or grams per plant, adjusted for grain moisture level at harvest.

As used herein, "sequence identity" or "identity" in the context of two polynucleotides or polypeptide sequences refer to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" is calculated by determining the number of positions at which the identical nucleic acid base or amino acid residue occurs in both sequences to yield the number of matched positions, dividing the number of matched positions by the total number of positions in the window of comparison, and multiplying the result by 100.

Unless stated otherwise, multiple alignments of the sequences provided herein are performed using the Clustal V method of alignment (Higgins and Sharp. (1989) *CABIOS*. 5:151-153) with the default parameters (GAP PENALTY=10, GAP LENGTH PENALTY=10). Default parameters for pairwise alignments and calculation of percent identity of amino acid sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Compositions

A. Polynucleotides and Polypeptides

The present disclosure provides polynucleotides encoding the following polypeptides:

One aspect of the disclosure provides a polynucleotide encoding a polypeptide comprising an amino acid sequence that is at least 80% identical (e.g. 81%, 82%, 83%, 84%, 85%, 86%, 87%, 88%, 89%, 90%, 91%, 92%, 93%, 94%, 95%, 96%, 97%, 98%, 99%, or 100%) to the amino acid sequence of any one of SEQ ID NO: 3 (OsLNTP12), SEQ ID NO: 6 (OsLNTP13), SEQ ID NO: 9 (OsGRRP1), SEQ ID NO: 12 (OsLNTP14), SEQ ID NO: 15 (OsLNTP15), SEQ ID NO: 18 (OsLNTP16), SEQ ID NO: 21 (OsLNTP17) and SEQ ID NO: 24 (OsPTR11).

"OsLNTP12" refers to a rice polypeptide that confers a low nitrogen tolerance phenotype when overexpressed. The OsLNTP12 polypeptide (SEQ ID NO: 3) is encoded by the coding sequence (CDS) (SEQ ID NO: 2) or nucleotide sequence (SEQ ID NO: 1) at rice gene locus LOC_Os01g16280.1, which is annotated as "Expressed protein" in TIGR. "LNTP12 polypeptide" refers herein to the OsLNTP12 polypeptide and its paralogs (e.g., SEQ ID NO: 48 encoded by SEQ ID NO: 47) or homologs from other organisms.

"OsLNTP13" refers to a rice polypeptide that confers a low nitrogen tolerance phenotype when overexpressed. The OsLNTP13 polypeptide (SEQ ID NO: 6) is encoded by the coding sequence (CDS) (SEQ ID NO: 5) or nucleotide sequence (SEQ ID NO: 4) at rice gene locus LOC_Os09g29880.1, which is annotated as "Expressed protein" in TIGR. "LNTP13 polypeptide" refers herein to the OsLNTP13 polypeptide and its paralogs (e.g., SEQ ID NO: 50 encoded by SEQ ID NO: 49) or homologs from other organisms.

"OsGRRP1" refers to a rice polypeptide that confers a low nitrogen tolerance phenotype when overexpressed. The OsGRRP1 polypeptide (SEQ ID NO: 9) is encoded by the coding sequence (CDS) (SEQ ID NO: 8) or nucleotide sequence (SEQ ID NO: 7) at rice gene locus LOC_Os09g32320.1, which is annotated as "Expressed protein" in TIGR. "GRRP1 polypeptide" refers herein to the OsGRRP1 polypeptide and its paralogs or homologs from other organisms, such as maize (e.g., SEQ ID NO: 52 encoded by SEQ ID NO: 51).

"OsLNTP14" refers to a rice polypeptide that confers a low nitrogen tolerance phenotype when overexpressed. The OsLNTP14 polypeptide (SEQ ID NO: 12) is encoded by the coding sequence (CDS) (SEQ ID NO: 11) or nucleotide sequence (SEQ ID NO: 10) at rice gene locus LOC_Os11g33380.1, which is annotated as "Expressed protein" in TIGR. "LNTP14 polypeptide" refers herein to the OsLNTP14 polypeptide and its paralogs (e.g., SEQ ID NO: 54 encoded by SEQ ID NO: 53) or homologs from other organisms, such as maize (e.g., SEQ ID NO: 56 encoded by SEQ ID NO: 55).

"OsLNTP15" refers to a rice polypeptide that confers a low nitrogen tolerance phenotype when overexpressed. The OsLNTP15 polypeptide (SEQ ID NO: 15) is encoded by the coding sequence (CDS) (SEQ ID NO: 14) or nucleotide sequence (SEQ ID NO: 13) at rice gene locus LOC_Os09g32310.1, which is annotated as "Expressed protein" in TIGR. "LNTP15 polypeptide" refers herein to the OsLNTP15 polypeptide and its paralogs (e.g., SEQ ID NO: 58 encoded by SEQ ID NO: 57) or homologs from other organisms.

"OsLNTP16" refers to a rice polypeptide that confers a low nitrogen tolerance phenotype when overexpressed. The OsLNTP16 polypeptide (SEQ ID NO: 18) is encoded by the coding sequence (CDS) (SEQ ID NO: 17) or nucleotide sequence (SEQ ID NO: 16) at rice gene locus LOC_Os04g32004.1, which is annotated as "Expressed protein" in TIGR. "LNTP16 polypeptide" refers herein to the OsLNTP16 polypeptide and its paralogs or homologs from other organisms.

"OsLNTP17" refers to a rice polypeptide that confers a low nitrogen tolerance phenotype when overexpressed. The OsLNTP17 polypeptide (SEQ ID NO: 21) is encoded by the coding sequence (CDS) (SEQ ID NO: 20) or nucleotide sequence (SEQ ID NO: 19) at rice gene locus LOC_Os02g46530.1, which is annotated as "Expressed protein" in TIGR. "LNTP17 polypeptide" refers herein to the OsLNTP17 polypeptide and its paralogs or homologs from other organisms.

"OsPTR11" refers to a rice polypeptide that confers a low nitrogen tolerance phenotype when overexpressed. The OsPTR11 polypeptide (SEQ ID NO: 24) is encoded by the coding sequence (CDS) (SEQ ID NO: 23) or nucleotide sequence (SEQ ID NO: 22) at rice gene locus LOC_Os10g02340.1, which is annotated as "Expressed protein" in TIGR. "PTR11 polypeptide" refers herein to the OsPTR11 polypeptide and its paralogs (e.g., SEQ ID NO: 60 encoded by SEQ ID NO: 59) or homologs from other organisms, such as maize (e.g., SEQ ID NO: 62 encoded by SEQ ID NO: 61).

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

B. Recombinant DNA Constructs

Also provided are recombinant DNA constructs comprising any of the polynucleotides described herein. In certain embodiments, the recombinant DNA construct further comprises at least one regulatory element. In certain embodiments the at least one regulatory element is a heterologous regulatory element. In certain embodiments, the at least one regulatory element of the recombinant DNA construct comprises a promoter. In certain embodiments, the promoter is a heterologous promoter.

A number of promoters can be used in the recombinant DNA constructs of the present disclosure. The promoters can be selected based on the desired outcome, and may include constitutive, tissue-specific, inducible, or other promoters for expression in the host organism.

A "constitutive" promoter is a promoter, which is active under most environmental conditions. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

A tissue-specific or developmentally-regulated promoter is a DNA sequence which regulates the expression of a DNA sequence selectively in the cells/tissues of a plant, such as in those cells/tissues critical to tassel development, seed set, or both, and which usually limits the expression of such a DNA sequence to the developmental period of interest (e.g. tassel development or seed maturation) in the plant. Any identifiable promoter which causes the desired temporal and spatial expression may be used in the methods of the present disclosure.

Many leaf-preferred promoters are known in the art (Yamamoto et al. (1997) Plant J. 12 (2):255-265; Kwon et al. (1994) Plant Physiol. 105:357-367; Yamamoto et al. (1994) Plant Cell Physiol. 35 (5):773-778; Gotor et al. (1993) Plant J. 3:509-518; Orozco et al. (1993) Plant Mol. Biol. 23 (6):1129-1138; and Matsuoka et al. (1993) Proc. Natl. Acad. Sci. USA 90 (20):9586-9590).

Promoters which are seed or embryo-specific and may be useful in the disclosure include soybean Kunitz trypsin inhibitor (Kti3, Jofuku and Goldberg. (1989) Plant Cell 1:1079-1093), convicilin, vicilin, and legumin (Pea cotyledons) (Rerie, W. G., et al. (1991) Mol. Gen. Genet. 259: 149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564). Promoters of seed-specific genes operably linked to heterologous coding regions in chimeric gene constructions maintain their temporal and spatial expression pattern in transgenic plants. Such examples include Arabidopsis 2S seed storage protein gene promoter to express enkephalin peptides in Arabidopsis and Brassica napus seeds (Vanderkerckhove et al. (1989) Bio/Technology 7: L929-932), bean lectin and bean beta-phaseolin promoters to express luciferase (Riggs et al. (1989) Plant Sci. 63:47-57), and wheat glutenin promoters to express chloramphenicol acetyl transferase (Colot et al. (1987) EMBO J 6:3559-3564).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Also contemplated are synthetic promoters which include a combination of one or more heterologous regulatory elements.

The promoter of the recombinant DNA constructs of the invention can be any type or class of promoter known in the art, such that any one of a number of promoters can be used to express the various polynucleotide sequences disclosed herein, including the native promoter of the polynucleotide sequence of interest. The promoters for use in the recombinant DNA constructs of the invention can be selected based on the desired outcome.

The recombinant DNA constructs of the present disclosure may also include other regulatory elements, including but not limited to, translation leader sequences, introns, and polyadenylation recognition sequences. In certain embodiments, a recombinant DNA construct further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg. (1988) Mol Cell Biol. 8:4395-4405; Callis et al. (1987) Genes Dev. 1:1183-1200).

C. Plants and Plant Cells

Provided are plants, plant cells, plant parts, seed and grain comprising in its genome any of the recombinant DNA constructs described herein, so that the plants, plant cells, plant parts, seed, and/or grain have increased expression of the encoded polypeptide.

Also provided are plants, plant cells, plant parts, seeds, and grain comprising an introduced genetic modification at a genomic locus that encodes a polypeptide comprising an amino acid sequence that is at least 80% identical to an amino acid sequence selected from the group consisting of SEQ ID NOs: 3, 6, 9, 12, 15, 18, 21 or 24. In certain embodiments, the genetic modification increases the activity of the encoded polypeptide. In certain embodiments, the genetic modification increases the level of the encoded polypeptide. In certain embodiments, the genetic modification increases both the level and activity of the encoded polypeptide.

The plant may be a monocotyledonous or dicotyledonous plant, for example, a rice or maize or soybean plant, such as a maize hybrid plant or a maize inbred plant. The plant may also be sunflower, sorghum, canola, wheat, alfalfa, cotton, barley, millet, sugar cane or switchgrass.

In certain embodiments the plant exhibits increased nitrogen stress tolerance when compared to a control plant. In certain embodiments, the plant exhibits an alteration of at least one agronomic characteristic when compared to the control plant.

One of ordinary skill in the art is familiar with protocols for simulating low nitrogen conditions and for evaluating nitrogen stress tolerance of plants that have been subjected to simulated or naturally-occurring nitrogen stress conditions.

D. Stacking With Other Traits of Interest

In some embodiments, the inventive polynucleotides disclosed herein are engineered into a molecular stack. Thus, the various host cells, plants, plant cells, plant parts, seeds, and/or grain disclosed herein can further comprise one or more traits of interest. In certain embodiments, the host cell, plant, plant part, plant cell, seed, and/or grain is stacked with any combination of polynucleotide sequences of interest in order to create plants with a desired combination of traits. As used herein, the term "stacked" refers to having multiple traits present in the same plant or organism of interest. For example, "stacked traits" may comprise a molecular stack where the sequences are physically adjacent to each other. A trait, as used herein, refers to the phenotype derived from a particular sequence or groups of sequences. In one embodiment, the molecular stack comprises at least one polynucleotide that confers tolerance to glyphosate. Polynucleotides that confer glyphosate tolerance are known in the art.

In certain embodiments, the molecular stack comprises at least one polynucleotide that confers tolerance to glyphosate and at least one additional polynucleotide that confers tolerance to a second herbicide.

In certain embodiments, the plant, plant cell, seed, and/or grain having an inventive polynucleotide sequence may be stacked with, for example, one or more sequences that confer tolerance to: an ALS inhibitor; an HPPD inhibitor; 2,4-D; other phenoxy auxin herbicides; aryloxyphenoxypropionate herbicides; dicamba; glufosinate herbicides; herbicides which target the protox enzyme (also referred to as "protox inhibitors").

The plant, plant cell, plant part, seed, and/or grain having an inventive polynucleotide sequence can also be combined with at least one other trait to produce plants that further comprise a variety of desired trait combinations. For instance, the plant, plant cell, plant part, seed, and/or grain having an inventive polynucleotide sequence may be stacked with polynucleotides encoding polypeptides having pesticidal and/or insecticidal activity, or a plant, plant cell, plant part, seed, and/or grain having an inventive polynucleotide sequence may be combined with a plant disease resistance gene.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Methods

Provided is a method for increasing nitrogen stress tolerance and/or grain yield in a plant, comprising increasing the expression of at least one polynucleotide encoding a polypeptide with amino acid sequence of at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 3, 6, 9, 12, 15, 18, 21 or 24.

In certain embodiments, the method comprises: (a) expressing in a regenerable plant cell a recombinant DNA construct comprising a regulatory element operably linked to the polynucleotide encoding the polypeptide; and (b) generating the plant, wherein the plant comprises in its genome the recombinant DNA construct. In certain embodiments the regulatory element is a heterologous promoter.

In certain embodiments, the method comprises: (a) introducing in a regenerable plant cell a targeted genetic modification at a genomic locus that encodes the polypeptide; and (b) generating the plant, wherein the level and/or activity of the encoded polypeptide is increased in the plant. In certain embodiments the targeted genetic modification is introduced using a genome modification technique selected from the group consisting of a polynucleotide-guided endonuclease, CRISPR-Cas endonucleases, base editing deaminases, a zinc finger nuclease, a transcription activator-like effector nuclease (TALEN), engineered site-specific meganucleases, or Argonaute. In certain embodiments, the targeted genetic modification is present in (a) the coding region; (b) a non-coding region; (c) a regulatory sequence; (d) an untranslated region; or (e) any combination of (a)-(d) of the genomic locus that encodes a polypeptide comprising an amino acid sequence that is at least 80% identical to an amino acid sequence selected from the group consisting of SEQ ID NOs: 3, 6, 9, 12, 15, 18, 21 or 24.

In certain embodiments the DNA modification is an insertion of one or more nucleotides, preferably contiguous, in the genomic locus. For example, the insertion of an expression modulating element (EME), such as an EME described in PCT/US2018/025446, in operable linkage with the gene. In certain embodiments, the targeted DNA modification may be the replacement of the endogenous polypeptide promoter with another promoter known in the art to have higher expression. In certain embodiments, the targeted DNA modification may be the insertion of a promoter known in the art to have higher expression into the 5'UTR so that expression of the endogenous polypeptide is controlled by the inserted promoter. In certain embodiments, the DNA modification is a modification to optimize Kozak context to increase expression. In certain embodiments, the DNA modification is a polynucleotide modification or SNP at a site that regulates the stability of the expressed protein.

The plant for use in the inventive methods can be any plant species described herein. In certain embodiments, the plant is maize, soybean, or rice.

Various methods can be used to introduce a sequence of interest into a plant, plant part, plant cell, seed, and/or grain. "Introducing" is intended to mean presenting to the plant, plant cell, seed, and/or grain the inventive polynucleotide or resulting polypeptide in such a manner that the sequence gains access to the interior of a cell of the plant. The methods of the disclosure do not depend on a particular method for introducing a sequence into a plant, plant cell, seed, and/or grain, only that the polynucleotide or polypeptide gains access to the interior of at least one cell of the plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In other embodiments, the inventive polynucleotides disclosed herein may be introduced into plants by contacting plants with a virus or viral nucleic acids. Generally, such methods involve incorporating a nucleotide construct of the disclosure within a DNA or RNA molecule. It is recognized that the inventive polynucleotide sequence may be initially synthesized as part of a viral polyprotein, which later may be processed by proteolysis in vivo or in vitro to produce the desired recombinant protein. Further, it is recognized that promoters disclosed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a polynucleotide disclosed herein, for example, as part of an expression cassette, stably incorporated into their genome.

Transformed plant cells which are derived by plant transformation techniques, including those discussed above, can be cultured to regenerate a whole plant which possesses the transformed genotype (i.e., an inventive polynucleotide), and thus the desired phenotype, such as increased yield. For transformation and regeneration of maize see, Gordon-Kamm et al., *The Plant Cell*, 2:603-618 (1990).

Various methods can be used to introduce a genetic modification at a genomic locus that encodes a polypeptide disclosed herein into the plant, plant part, plant cell, seed, and/or grain. In certain embodiments the targeted DNA modification is through a genome modification technique selected from the group consisting of a polynucleotide-guided endonuclease, CRISPR-Cas endonucleases, base editing deaminases, zinc finger nuclease, a transcription activator-like effector nuclease (TALEN), engineered site-specific meganuclease, or Argonaute.

In some embodiments, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to, transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

In addition to modification by a double strand break technology, modification of one or more bases without such double strand break are achieved using base editing technology, see e.g., Gaudelli et al., (2017) Programmable base editing of A*T to G*C in genomic DNA without DNA cleavage. Nature 551 (7681):464-471; Komor et al., (2016) Programmable editing of a target base in genomic DNA without double-stranded DNA cleavage, Nature 533 (7603): 420-4.

These fusions contain dCas9 or Cas9 nickase and a suitable deaminase, and they can convert e.g., cytosine to uracil without inducing double-strand break of the target DNA. Uracil is then converted to thymine through DNA replication or repair. Improved base editors that have targeting flexibility and specificity are used to edit endogenous locus to create target variations and improve grain yield. Similarly, adenine base editors enable adenine to inosine change, which is then converted to guanine through repair or replication. Thus, targeted base changes i.e., C•G to T•A conversion and A•T to G•C conversion at one more location made using appropriate site-specific base editors.

In an embodiment, base editing is a genome editing method that enables direct conversion of one base pair to another at a target genomic locus without requiring double-stranded DNA breaks (DSBs), homology-directed repair (HDR) processes, or external donor DNA templates. In an embodiment, base editors include (i) a catalytically impaired CRISPR-Cas9 mutant that are mutated such that one of their nuclease domains cannot make DSBs; (ii) a single-strand-specific cytidine/adenine deaminase that converts C to U or A to G within an appropriate nucleotide window in the single-stranded DNA bubble created by Cas9; (iii) a uracil glycosylase inhibitor (UGI) that impedes uracil excision and downstream processes that decrease base editing efficiency and product purity; and (iv) nickase activity to cleave the non-edited DNA strand, followed by cellular DNA repair processes to replace the G-containing DNA strand.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism (Miller et al. (2011) Nature Biotechnology 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3-finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

EXAMPLES

The following are examples of specific embodiments of some aspects of the invention. The examples are offered for illustrative purposes only and are not intended to limit the scope of the invention in any way.

Example 1

Cloning and Vector Construction of Nitrogen Stress Tolerance Genes

A binary construct that contains four multimerized enhancers elements derived from the Cauliflower Mosaic Virus 35S (CaMV 35S) promoter was used, and the rice activation tagging population was developed from four japonica (*Oryza sativa* ssp. *Japonica*) varieties (Zhonghua 11, Chaoyou 1, Taizhong 65 and Nipponbare), which were transformed by the *Agrobacteria*-mediated transformation method as described by Lin and Zhang ((2005) *Plant Cell Rep.* 23:540-547). The transgenic lines generated were developed and the transgenic seeds were harvested to form the rice activation tagging population.

Nitrogen stress tolerance tagging lines (ATLs) were confirmed in repeated field experiments and their T-DNA insertion loci were determined. The genes near the left border and right border of the T-DNA were cloned and the functional genes were recapitulated by field screens. Only the recapitulated functional genes are showed herein. And based on LOC IDs of these genes shown in Table 2, primers were designed for cloning the rice nitrogen stress tolerance genes OsLNTP12, OsLNTP13, OsGRRP1, OsLNTP14, OsLNTP15, OsLNTP16, OsLNTP17, OsPTR11.

TABLE 2

Rice gene names, Gene IDs (from TIGR) and Construct IDs

| Gene name | LOC ID | Construct ID |
|---|---|---|
| OsLNTP12 | LOC_Os01g16280.1 | DP1002 |
| OsLNTP13 | LOC_Os09g29880.1 | DP1554 |
| OsGRRP1 | LOC_Os09g32320.1 | DP1227 |
| OsLNTP14 | LOC_Os11g33380.1 | DP1167 |
| OsLNTP15 | LOC_Os09g32310.1 | DP1226 |
| OsLNTP16 | LOC_Os04g32004.1 | DP1833 |
| OsLNTP17 | LOC_Os02g46530.1 | DP2194 |
| OsPTR11 | LOC_Os10g02340.1 | DP0914 |

PCR amplified products were extracted after the agarose gel electrophoresis using a column kit and then ligated with TA cloning vectors. The sequences and orientation in these constructs were confirmed by sequencing. Each gene was cloned into a plant binary construct.

Example 2

Transformation and Gene Expression Analysis of Transgenic Rice Lines

Zhonghua 11 (*Oryza sativa* L.) were transformed with either a vector prepared in Example 1 or an empty vector (DP0158) by *Agrobacteria*-mediated transformation as described by Lin and Zhang ((2005) *Plant Cell Rep.* 23:540-547). Transgenic seedlings (T$_0$) generated in the transformation laboratory were transplanted in field to get T$_1$ seeds. The T$_1$ and subsequent T$_2$ seeds were screened to confirm transformation and positively identified transgenic seeds were used in the following trait screens.

The gene expression levels in the leaves of the transgenic rice plants were determined by RT-PCR. Primers were designed for the RT-PCR for OsLNTP12, OsLNTP15, and OsPTR11 genes in the over-expression transgenic rice. The level of expression in ZH11-TC (tissue cultured ZH11 rice) was set at 1.00, and the expression levels in the DP1002, DP1226 and DP0914-transgenic rice plants were compared to ZH11-TC. Gene expression was normalized based on the EF-1α mRNA levels, and the results from the gene expression analysis are provided in Table 3 below.

TABLE 3

Relative Expression Level Fold Increase in Transgenic Rice Plants

| Gene name | Construct ID | Relative Expression Level Fold Increase |
|---|---|---|
| OsLNTP12 | DP1002 | From 1004.58 to 2328.36 |
| OsLNTP15 | DP1226 | From 2.18 to 7724.55 |
| OsPTR11 | DP0914 | From 159.35 to 1135.97 |

Example 3

Characterization of the Transgenic Rice Plants

The transgenic rice plants from Example 2 and ZH11-TC and DP0158 rice plants were tested for: (a) low nitrogen tolerance/nitrogen use efficiency, (b) cholate sensitivity.

T$_2$ seeds from the plants of Example 2 were sterilized by 800 ppm carbendazol for 8 hours at 32° C. and washed 3-5 time, soaked in water for 16 hours at 32° C., and germinated for 18 hours at 35-37° C. in an incubator. Germinated seeds were used as follows for each test:

(a) low nitrogen tolerance/nitrogen use efficiency—Two nitrogen levels: N-0 (using fertilizer without nitrogen) and N-1 (with normal fertilizer) were set in the experiment. Germinated seeds were planted in a seedbed field. At 3-leaf stage, the seedlings were transplanted into the testing field with 4 replicates and 10 plants per replicate for each transgenic line, and the 4 replicates were planted in the same block. The ZH11-TC and DP0158 plants were planted nearby the transgenic lines in the same block, and were used as controls in the statistical analysis. The rice plants were managed by normal practice using pesticides, but applying phosphorous fertilizer and potassium fertilizer for N-0 treatment and normal fertilizer for N-1 treatment.

At the end of the season, six representative plants of each transgenic line were harvested from the middle of the row per line and grain yield per plant was measured. The grain yield per plant data were statistically analyzed using mixed linear model by ASReml program. Positive transgenic lines are selected based on the analysis (P<0.1).

(b) cholate sensitivity—this assay was performed in culture room kept temperature at 28-30° C. and humidity around ~30%. The germinated seeds were placed in a tube with a hole at the bottom, and water cultured at 30° C. for 6 days till one-leaf and one-terminal bud stage. Uniform seedlings about 5.5 cm in height were selected for chlorate screening. Randomized block design was used in this experiment. There are five blocks in one screened container. Each transgenic line was placed in one row (12 plants/line), and ZH11-TC seedlings were placed in 3 rows (31*2 plants) randomly in one block. Then the seedlings were treated with 0.4 mM chlorate in concentration for 3-5 days at 10 h day/14 h night, the treated seedlings first encountered night and absorb the chlorate solution which was changed at the third day. After treated for 5 days, the seedlings were then cultured in 1/10 Hoagland's solution for 4 days. The seedlings with withered leaves and totally without green are counted as sensitive; while the seedlings only with necrosed leaves or stem, or bleached leaves are not considered to be sensitive seedlings.

Sensitive rate was used as a parameter to for this assay, which is the percentage of the number of sensitive plants over the total plant number. The data was analyzed using a statistic model of "Y~seg+line (seg)+rep+error" with random effect of "rep" and Statistic Method of "SAS Proc Glimmix".

The results from these studies are provided in Table 4, which provides the combined data of the transgenic lines for each of the constructs.

TABLE 4

Agronomic Characteristics of the Transgenic Rice Plants

| No | Construct ID | Avg. yield per plant under field low nitrogen conditions (g/plant) | Avg. yield per plant under field normal nitrogen conditions (g/plant) | Avg. chlorate sensitive rate (%) |
|---|---|---|---|---|
| 1 | ZH11-TC | 20.48 ± 1.15 | 28.50 ± 0.72 | |
|   | DP0158 | 22.20 ± 1.14 | 31.02 ± 0.73 | |
|   | DP1002 | 23.26 ± 1.14$^{a,\,b}$ | 32.23 ± 0.73$^{a,\,b}$ | |
| 2 | ZH11-TC | 20.55 ± 1.04 | 28.80 ± 0.86 | 26% |
|   | DP0158 | 22.13 ± 1.03 | 31.14 ± 0.88 | 29% |
|   | DP1554 | 23.51 ± 1.02$^{a,\,b}$ | 33.50 ± 0.86$^{a,\,b}$ | 43%$^{m,\,n}$ |
| 3 | ZH11-TC | 20.48 ± 1.14 | 28.37 ± 0.67 | |
|   | DP0158 | 22.09 ± 1.14 | 30.23 ± 0.74 | |
|   | DP1227 | 23.25 ± 1.14$^{a,\,b}$ | 31.37 ± 0.69$^{a,\,b}$ | |
| 4 | ZH11-TC | 20.54 ± 0.84 | 24.46 ± 0.97 | 17% |
|   | DP0158 | 19.57 ± 0.84 | 22.21 ± 0.97 | 37% |
|   | DP1167 | 23.51 ± 1.41$^{a,\,b}$ | 27.07 ± 1.66$^{a,\,b}$ | 69%$^{m,\,n}$ |
| 5 | ZH11-TC | 34.70 ± 2.46 | | |
|   | DP0158 | 31.12 ± 2.46 | | |
|   | DP1226 | 35.96 ± 1.93$^{b}$ | | |
| 6 | ZH11-TC | 33.24 ± 2.36 | 27.20 ± 0.68 | |
|   | DP0158 | 31.34 ± 2.35 | 24.90 ± 0.67 | |
|   | DP1833 | 35.44 ± 1.86$^{b}$ | 29.04 ± 1.52$^{b}$ | |
| 7 | ZH11-TC | 20.54 ± 0.84 | 23.72 ± 0.94 | |
|   | DP0158 | 19.57 ± 0.84 | 22.19 ± 0.93 | |
|   | DP2194 | 20.09 ± 1.26 | 26.97 ± 1.56$^{a,\,b}$ | |
| 8 | ZH11-TC | 20.48 ± 1.14 | 28.88 ± 0.85 | |
|   | DP0158 | 22.09 ± 1.14 | 30.75 ± 0.86 | |
|   | DP0914 | 23.10 ± 1.16$^{a}$ | 33.22 ± 0.83$^{a,\,b}$ | |

$^{a}$ P ≤ 0.1 compared to ZH11-TC control in field;
$^{b}$ P ≤ 0.1 compared to DP0158 control in field.
$^{m}$ P ≤ 0.05 compared to ZH11-TC control in Lab;
$^{n}$ P ≤ 0.05 compared to DP0158 control in Lab.

DP1002-transgenic rice plants were tested three times under field low nitrogen conditions and/or field normal nitrogen conditions in Beijing in three years. Two of them consistently showed that the average yield per plant of DP1002-transgenic rice plants increased under field low nitrogen and normal nitrogen conditions. As shown in table 4, four lines were tested under field low nitrogen and normal nitrogen conditions. Under field low nitrogen conditions, 1 of 4 line showed significantly increased the yield than that of DP0158 control, and 4 of 4 lines showed significantly increased the yield than that of ZH11-TC control. The average yield per plant of these 4 lines is 14% and 5% higher than that of ZH11-TC and DP0158 controls, respectively. While, under field normal nitrogen conditions, 2 of 4 lines showed significantly increased the yield than that of DP0158 control, and 4 of 4 lines showed significantly increased the yield than that of ZH11-TC control. The average yield per plant of these 4 lines is 13% and 4% higher than that of ZH11-TC and DP0158 controls, respectively. These results show that OsLNTP12 transgenic rice may have increased low nitrogen tolerance and/or nitrogen use efficiency.

DP1554-transgenic rice plants were tested three times under field low nitrogen conditions and/or field normal nitrogen conditions in Beijing in three years. Two of them consistently showed that the average yield per plant of DP1554-transgenic rice plants increased under field low nitrogen and normal nitrogen conditions. As shown in table 4, five lines were tested under field low nitrogen and normal nitrogen conditions. Under field low nitrogen conditions, 3 of 5 lines showed significantly increased the yield than that of DP0158 control, and 4 of 5 lines showed significantly increased the yield than that of ZH11-TC control. The average yield per plant of these 5 lines is 14% and 6% higher than that of ZH11-TC and DP0158 controls, respectively. While, under field normal nitrogen conditions, 3 of 5 lines showed significantly increased the yield than that of DP0158 control, and 4 of 5 lines showed significantly increased the yield than that of ZH11-TC control. The average yield per plant of these 5 lines is 16% and 8% higher than that of ZH11-TC and DP0158 controls, respectively. DP1554-transgenic rice plants were also tested two times in chlorate assays. Consistently results were obtained. In the first experiment, ten lines were tested, and the average chlorate sensitive rate of all DP1554-transgenic lines (43%) was significantly greater than that of ZH11-TC (26%) and DP0158 (29%) controls at construct level. At transgenic line level, 6 of 10 lines had significantly greater sensitive rates than that of ZH11-TC and DP0158 controls (Table 4). These results demonstrate that OsLNTP13 may increase the nitrogen use efficiency and/or low nitrogen tolerance of transgenic plants and increase the chlorate sensitivity of transgenic plants compared to both controls.

DP1227-transgenic rice plants were tested three times under field low nitrogen conditions and/or field normal nitrogen conditions in Beijing in three years. All experiments consistently showed that the average yield per plant of DP1227-transgenic rice plants increased under field low nitrogen and field normal nitrogen conditions. As shown in table 4, under field low nitrogen conditions, 1 of 4 line showed significantly increased the yield than that of DP0158 control, and 2 of 4 lines showed significantly increased the yield than that of ZH11-TC control. The average yield per plant of these 4 lines is 14% and 5% higher than that of ZH11-TC and DP0158 controls, respectively. While, under field normal nitrogen conditions, 2 of 4 lines showed significantly increased the yield than that of DP0158 control, and 3 of 4 lines showed significantly increased the yield than that of ZH11-TC control. The average yield per plant of these 4 lines is 11% and 4% higher than that of ZH11-TC and DP0158 controls, respectively. These results demonstrate that OsGRRP1 may increase the nitrogen use efficiency and/or low nitrogen tolerance of transgenic rice plants compared to both controls.

DP1167-transgenic rice plants were tested two times under field low nitrogen conditions and/or field normal nitrogen conditions in Beijing in two years. All experiments consistently showed that the average yield per plant of DP1167-transgenic rice plants increased under field low nitrogen and field normal nitrogen conditions. As shown in table 4, seven lines were tested under field low nitrogen and normal nitrogen conditions. Under field low nitrogen conditions, 7 of 7 lines showed significantly increased the yield than that of DP0158 control, and 3 of 7 lines showed significantly increased the yield than that of ZH11-TC control. The average yield per plant of these 7 lines is 14% and 20% higher than that of ZH11-TC and DP0158 controls, respectively. While, under field normal nitrogen conditions, 6 of 6 lines showed significantly increased the yield than that of DP0158 control, and 1 of 6 line showed significantly increased the yield than that of ZH11-TC control. The average yield per plant of these 6 lines is 11% and 22% higher than that of ZH11-TC and DP0158 controls, respectively. DP1167-transgenic rice plants were also tested two times in chlorate assays. Consistently results were obtained. In the second experiment, the average chlorate sensitive rate of all DP1167-transgenic lines (69%) was significantly greater than that of ZH11-TC (17%) and DP0158 (37%) controls at construct level. At transgenic line level, all ten lines had significantly greater sensitive rates than that of ZH11-TC and DP0158 controls (Table 4). These results demonstrate that OsLNTP14 may increase the nitrogen use efficiency and/or low nitrogen tolerance of transgenic plants and increase the chlorate sensitivity of transgenic plants compared to both controls.

DP1226-transgenic rice plants were tested two times under field low nitrogen conditions in Beijing in two years. All experiments consistently showed that the average yield per plant of DP1226-transgenic rice plants increased under field low nitrogen conditions. As shown in table 4, under field low nitrogen conditions, 7 of 7 lines showed significantly increased the yield than that of DP0158 control. All lines also showed increased the yield than that of ZH11-TC control but not to a significant degree. The average yield per plant of these 7 lines is 4% and 16% higher than that of ZH11-TC and DP0158 controls, respectively. These results demonstrate that OsLNTP15 may increase the low nitrogen tolerance of transgenic plants compared to both controls.

DP1833-transgenic rice plants were tested two times under field low nitrogen conditions or field normal nitrogen conditions in Beijing in two years. Two of them consistently showed that the average yield per plant of DP1833-transgenic rice plants increased under field low nitrogen and field normal nitrogen conditions. As shown in table 4, eight lines were tested under field low nitrogen conditions, 6 of 8 lines showed significantly increased the yield than that of DP0158 control, and 7 of 8 lines showed increased the yield than that of ZH11-TC control but not to a significant degree. The average yield per plant of these 8 lines is 7% and 13% higher than that of ZH11-TC and DP0158 controls, respectively. In another year, seven lines were tested again under field normal nitrogen conditions, and 5 of 7 lines showed significantly increased the yield than that of DP0158 control, and 1 of 7 line showed significantly increased the yield than that of ZH11-TC control. The average yield per plant of these 7 lines is 7% and 17% higher than that of ZH11-TC and DP0158 controls, respectively. These results show that OsLNTP16 transgenic rice may have increased low nitrogen tolerance and/or nitrogen use efficiency.

DP2194-transgenic rice plants were tested two times under field low nitrogen conditions and/or field normal nitrogen conditions in Beijing in two years. Two of them consistently showed that the average yield per plant of DP2194-transgenic rice plants increased under field low nitrogen and normal nitrogen conditions. As shown in table 4, twelve lines were tested under field low nitrogen conditions, 3 of 12 lines showed increased the yield than that of ZH11-TC and DP0158 controls, but not to a significant degree. While, under field normal nitrogen conditions, and 6 of 7 lines showed significantly increased the yield than that of DP0158 control, and 3 of 7 lines showed significantly increased the yield than that of ZH11-TC control. The average yield per plant of these 7 lines is 14% and 22% higher than that of ZH11-TC and DP0158 controls, respectively. These results show that OsLNTP17 transgenic rice may have increased nitrogen use efficiency under field normal nitrogen conditions.

DP0914-transgenic rice plants were tested three times under field low nitrogen conditions and/or field normal nitrogen conditions in Beijing in three years. Two of them consistently showed that the average yield per plant of DP0914-transgenic rice plants increased under field low nitrogen and normal nitrogen conditions. As shown in table 4, under the field low nitrogen conditions, 1 of 4 lines showed significantly increased yield than that of DP0158 control, and 4 of 4 lines showed significantly increased the yield than that of ZH11-TC control. The average yield per plant of these 4 lines is 13% and 5% higher than that of ZH11-TC and DP0158 controls, respectively. Under the field normal nitrogen conditions, 3 of 5 lines showed significantly increased yield than that of DP0158 control, and 5 of 5 lines showed significantly increased yield than that of ZH11-TC control. The average yield per plant of these 5 lines is 15% and 8% higher than that of ZH11-TC and DP0158 controls, respectively. These results show that OsPTR11 transgenic rice may have increased low nitrogen tolerance and/or nitrogen use efficiency.

Taken together, these results indicate that OsLNTP12, OsLNTP13, OsGRRP1, OsLNTP14, OsLNTP15, OsLNTP16, OsLNTP17 and OsPTR11-transgenic rice plants have increased low nitrogen tolerance and/or nitrogen use efficiency.

Example 4

Transformation and Evaluation of Maize with Rice Nitrogen Stress Tolerance Genes Maize plants can be transformed one of the polynucleotides encoding the polypeptides described herein or a corresponding homolog from maize, Arabidopsis, or other species. Expression of the gene in the maize transformation vector can be under control of a constitutive promoter such as the maize ubiquitin promoter (Christensen et al. (1989) Plant Mol. Biol. 12:619-632 and Christensen et al. (1992) Plant Mol. Biol. 18:675-689) or under control of another promoter, such as a stress-responsive promoter or a tissue-preferred promoter. The recombinant DNA construct can be introduced into maize cells by particle bombardment substantially as described in International Patent Publication WO 2009/006276. Alternatively, maize plants can be transformed with the recombinant DNA construct by Agrobacterium-mediated transformation substantially as described by Zhao et al. in Meth. Mol. Biol. 318:315-323 (2006) and in Zhao et al., Mol. Breed. 8:323-333 (2001) and U.S. Pat. No. 5,981,840 issued Nov. 9, 1999.

Progeny of the regenerated plants, such as $T_1$ plants, can be subjected to a soil-based nitrogen stress. Using image analysis, plant area, volume, growth rate and color can be measured at multiple times before and during nitrogen stress. Significant delay in wilting or leaf area reduction, a reduced yellow-color accumulation, and/or an increased growth rate during nitrogen stress, relative to a control, will be considered evidence that the gene functions in maize to enhance nitrogen stress tolerance and/or NUE.

What is claimed is:

1. A modified plant or seed comprising a polynucleotide encoding a polypeptide comprising an amino acid sequence that is at least 97% identical to SEQ ID NO: 12 operably linked to at least one heterologous regulatory element wherein the modified plant or seed comprises an increased expression of the polypeptide and improved nitrogen stress tolerance and/or nitrogen use efficiency (NUE) as compared to a control plant.

2. The plant of claim 1, wherein the plant comprises in its genome a recombinant DNA construct comprising the polynucleotide operably linked to the at least one heterologous regulatory element.

3. The plant of claim 1, wherein the plant comprises a targeted genetic modification at a genomic locus comprising a polynucleotide sequence encoding a polypeptide with an amino acid sequence of at least 97% sequence identity to SEQ ID NO: 12, thereby increasing expression of the polypeptide as compared to a control plant not comprising the targeted genetic modification.

4. The plant of claim 1, wherein said plant is selected from the group consisting of rice, maize, soybean, sunflower, sorghum, canola, wheat, alfalfa, cotton, barley, millet, sugar cane and switchgrass.

5. A method of increasing nitrogen stress tolerance or NUE in a plant, the method comprising:
(a) introducing in a regenerable plant cell a recombinant DNA construct comprising a regulatory element operably liked to a polynucleotide encoding a polypeptide comprising an amino acid sequence having at least 97% sequence identity to SEQ ID NO: 12; and
(b) generating the plant, wherein the plant comprises in its genome the recombinant DNA construct and has increased expression and/or activity of the polypeptide as compared to a control plant not comprising the recombinant DNA construct and wherein the plant has increased nitrogen stress tolerance or NUE as compared to the control plant.

6. A method of increasing nitrogen stress tolerance or NUE in a plant, the method comprising:
(a) introducing in a regenerable plant cell a targeted genetic modification at a genomic locus that encodes the polypeptide comprising an amino acid sequence of at least 97% sequence identity compared to SEQ ID NO: 12; and
(b) generating the plant, wherein the level and/or activity of the polypeptide is increased in the plant as compared to a control plant not comprising the targeted genetic modification and the plant has increased nitrogen stress tolerance or NUE as compared to the control plant.

7. The method of claim 6, wherein the targeted genetic modification is introduced using an enzyme selected from the group consisting of a polynucleotide-guided endonuclease, CRISPR-Cas endonucleases, base editing deaminases, a zinc finger nuclease, a transcription activator-like effector nuclease (TALEN), and engineered site-specific meganucleases.

8. The method of claim 6, wherein the targeted genetic modification is present in (a) the coding region; (b) a non-coding region; (c) a regulatory sequence; (d) an untranslated region; or (e) any combination of (a)-(d) of the genomic locus that encodes a polypeptide comprising an amino acid sequence that is at least 97% identical to an amino acid sequence selected from the group consisting of SEQ ID NOs: 12.

9. The method of claim 5, wherein the regulatory element is a heterologous promoter.

10. The modified plant or seed of claim 1, wherein the heterologous regulatory element is a heterologous promoter.

11. The method of claim 5, wherein said plant is selected from the group consisting of rice, maize, soybean, sunflower, sorghum, canola, wheat, alfalfa, cotton, barley, millet, sugar cane and switchgrass.

12. The method of claim 6, wherein said plant is selected from the group consisting of rice, maize, soybean, sunflower, sorghum, canola, wheat, alfalfa, cotton, barley, millet, sugar cane and switchgrass.

\* \* \* \* \*

SEQUENCE LISTING

<160> NUMBER OF SEQ ID NOS: 62

<210> SEQ ID NO 1
<211> LENGTH: 553
<212> TYPE: DNA
<213> ORGANISM: Oryza sativa

<400> SEQUENCE: 1

| | | | | | |
|---|---|---|---|---|---|
| cgaagagagg | agatcggcga | ggcaatggcg | ggtgatgggg | aggagaagga | catgaaggcg | 60 |
| gtggggagaa | ggaggacacg | acggtgtttg | gtgaggagga | ggacaacgcg | gaggcggtgg | 120 |
| ggaggaggcg | atgcagcagc | ggtgagtgcg | aaggaggacg | acgcggaagc | gatggggagg | 180 |
| aggcaatgca | gtagcgttgg | gtgggaggag | gagaacgcgg | cagcggtggc | aggtcaagga | 240 |
| gattcggcgg | cgcggggagt | ggcgggaagg | ggatcgagag | cggtagtagt | gagtagcacg | 300 |
| ggcgaagtct | tcgcgcggtg | atgggagcga | aaatcacggt | ggagatagga | tggagttgct | 360 |
| gtgcgagggt | gaatcgcagt | gtacggtagg | gatgagagcg | atgcggatga | gatgcagatg | 420 |
| gatggtagga | tcaacatgtt | gatttagcct | gtatgattgc | aaagagataa | ctcttttttt | 480 |
| tattagtaaa | tatttaaatg | gttatttagt | aattaattat | cattcttagg | catcagcgga | 540 |
| gccatatgtg | ttg | | | | | 553 |

<210> SEQ ID NO 2
<211> LENGTH: 276
<212> TYPE: DNA
<213> ORGANISM: Oryza sativa

<400> SEQUENCE: 2

| | | | | | |
|---|---|---|---|---|---|
| atggcgggtg | atggggagga | gaaggacatg | aaggcggtgg | ggagaaggag | gacacgacgg | 60 |
| tgtttggtga | ggaggaggac | aacgcggagg | cggtggggag | gaggcgatgc | agcagcggtg | 120 |
| agtgcgaagg | aggacgacgc | ggaagcgatg | gggaggagga | aatgcagtag | cgttgggtgg | 180 |
| gaggaggaga | acgcggcagc | ggtggcagtg | tacggtaggg | atgagagcga | tgcggatgag | 240 |
| atgcagatgg | atggtaggat | caacatgttg | atttag | | | 276 |

<210> SEQ ID NO 3
<211> LENGTH: 91
<212> TYPE: PRT
<213> ORGANISM: Oryza sativa

<400> SEQUENCE: 3

Met Ala Gly Asp Gly Glu Glu Lys Asp Met Lys Ala Val Gly Arg Arg
1               5                   10                  15

Arg Thr Arg Arg Cys Leu Val Arg Arg Thr Thr Arg Arg Arg Trp
        20                  25                  30

Gly Gly Gly Asp Ala Ala Ala Val Ser Ala Lys Glu Asp Asp Ala Glu
        35                  40                  45

Ala Met Gly Arg Arg Gln Cys Ser Ser Val Gly Trp Glu Glu Glu Asn
    50                  55                  60

Ala Ala Ala Val Ala Val Tyr Gly Arg Asp Glu Ser Asp Ala Asp Glu
65                  70                  75                  80

Met Gln Met Asp Gly Arg Ile Asn Met Leu Ile
                85                  90

<210> SEQ ID NO 4
<211> LENGTH: 3048
<212> TYPE: DNA
<213> ORGANISM: Oryza sativa

<400> SEQUENCE: 4

| | | | | | |
|---|---|---|---|---|---|
| attaaaactt | gacaatggtg | ggttgtgagc | acatggtttt | aaaggtcgtg | ctcatgacaa | 60 |
| ttaaggaccg | gttcgcgagc | tactgttgtg | agacattaac | tgtaccaacc | acaagccagc | 120 |

```
gtgggcaacg gctttacctt ttgtatagca tgattcattg tggggtgcca gactgagaag    180
cggcgagaag tccgtggggg gtcgctgggg agtccatgcc tctggttata tttatagagg    240
gggtgattat gatccaggaa tggtgcactg tggtgagttg tgttgtgctg agggtatttt    300
catagcctct attcaggtac tttccagtat cgcgacgcat ggtagacatg atgttgaggc    360
tgtgtcttgt gggtacagtg gtacacctct ggccaaagta aaactatttg aatagccgtg    420
cccgcggtta tgggcgggtt gagcaatgtt tttcgtgatt agtctcatac ctctcacaaa    480
aattattgat gctataactg gtaataattt gcttagcttc tggtttggag ttagatctgt    540
acaaccgggt atggttgttc aggatggttg ggcctgagca gtatgggtgt gctgttcagt    600
gttgattaaa attgatgatt aattactcta ctgttttact tctcttaaat gtttgctaaa    660
tgctgctttt gcaaatgagc ctatattatg ccaggtatcc ttgtacactt gcatatttgc    720
tgtgtgattt gttgagtatg tcatatgctc accttgcaat aatcaatcaa cctcctttga    780
agagaaagga tccagaagga gaagactttt ggcttatacc ccagttgagc tgcctgtggg    840
agtggagctg aattcatcgc tagaccgtta atccgttgct gttttctttt tcttttgtaa    900
gtatgcaacg ttattattat gatggatttg tatattaaat tgtcagtttg tgtacctcgg    960
ctgattccta gacgaggatt ttatgcacaa attagttcgg aaattactag tgaatttccg   1020
ggcttgacac tatccaacat ttattctttc agtgccgctt atctcgcttg gtgtggtctg   1080
taattcattt ggcttctaat ctgaaacctc ctcgcaatgt tggtcatatg tttgggagtt   1140
ggctatcatg tgtccccaaa gaaatgagga atctgctttt gatgggtgca acagctctgt   1200
gttggtccat ttggctaagt aggaatggag taatcaagat ggtgtcttct ccttcgcagg   1260
ttatcacctt agttacccgg tggctatgta cctgggctat cctccaccaa ccaggactgc   1320
gggatactat tacagtgata tctcgacagt tggaccaggt agtacatgag ttttttaccc   1380
aggagcatgg gtggcggtct agtctacgga ttgatagcta ttaagatata cggtggtatc   1440
tcgacagttg cagttggacc aggtggaaca ggagtttttt tacccaggaa catgggtgac   1500
ggtctagttt acggattgat agccaataag atatactctc tccattccaa attgatctac   1560
atattttata tgtagatcaa gaccaagaaa agctaataac tctctcatac tatatttact   1620
ctagcaacaa acttaatgca tgcaccatcc ccactatttt ctagccaata gcaaatcaag   1680
atattgcatt atgaatgaac acagatgtgt agatcattta ataataacct aaaaaaacta   1740
tatgtagatc aatttgtaat ggagggagta tgtttctgtc aaacttttgt actttggaga   1800
tgttctagtt gtttctttcc ttttttggct gtgtgtattt tatgcagagg ccggggtga    1860 cttagtttaa ttgtatcatt tttgatgtaa ttaattgagt ctaaataaag tttccattat   1920
ctcaaagggg agtactatct tctatttag attgagagaa ctgagaacat gataattctg    1980
tgagactctg ttcaaatttt cttctagcgg cacttcttcc ctatgtcgag cgacttcggc   2040
acagtggggg ccagccaagt gtaagctgtt tttatggctg gcactggcac ggttttgga    2100 tgcaacgcat ggatggacaa ccactcgttg tgtcattttt gtgcatagga ggagacggta   2160
aaccacatcc tgatcgagcg cgtctttgct cataaagttt ggctttacgt gctaaccttt   2220
ggcagaggcg acctttcgtc ggaccgacat gccctgcttc acgagtggtg gcactggcac   2280
ctttcgaggg gtcgactggg caagtagctc aaatgaggtt ttgatactcc catcgttctc   2340
gtctcttggc atcttcgcgt catcgacgat attctctctt aaatgccgta gatagtgttt   2400
ggttgtaaga atggttgtaa ggatgggata tgattgaata acatgggacg aatctacttt   2460
ttgagatgtt tgatttaagg gtgagtggga tgggttgatc cctggagaga aatattcctc   2520
```

```
tcagatccgg gaccaatcca tcctgcaaaa tctcgcggat gagctcgtct cacctggaac      2580
gggctcacgg cgtgaggcgc gccgcttcac cccgttcact cgctcgcact gtcccctttc      2640
actcacatcg tcgcactccg ctcgtgctcc tccgcccact gtgagtgatg acgatggcgg      2700
gctcgagcgg cagcaggcag ctcgggcgac gacgacgaat gggggcttgg cgacgacaga      2760
ttcggtgatg gggaggacgg cagcggcgaa tccagaggcg ggagggctg cgacggagga       2820 tctcgaggag gggagggctg cagcagcgga tccgaggcg aggagggcta cggcgacgac       2880
gggcgagggt gagtgcttcg acggtggcgg cggcaggagg cttggcaatg cggattcgg       2940 tggtgcggcg acgacgacga cgacgagtga gtgtgagtgc tccggctgcg gcagcgtcga     3000
tgacgatggt cgttgacggt ggttgcaaac gacgtccatc ccatctct                   3048
```

<210> SEQ ID NO 5
<211> LENGTH: 762
<212> TYPE: DNA
<213> ORGANISM: Oryza sativa

<400> SEQUENCE: 5

```
atggtgggtt gtgagcacat ggttttaaag gtcgtgctca tgacaattaa ggaccggttc        60
gcgagctact gttgttatca ccttagttac ccggtggcta tgtacctggg ctatcctcca       120
ccaaccagga ctgcgggata ctattacagt gatatctcga cagttggacc agcggcactt       180
cttccctatg tcgagcgact tcggcacagt gggggccagc caagtggtga gtgggatggg       240
ttgatccctg gagagaaata ttcctctcag atccggacc aatccatcct gcaaaatctc        300
gcggatgagc tcgtctcacc tggaacgggc tcacggcgtg aggcgcgccg cttcaccccg      360
ttcactcgct cgcactgtcc cctttcactc acatcgtcgc actccgctcg tgctcctccg      420
cccactgtga gtgatgacga tggcgggctc gagcggcagc aggcagctcg ggcgacgacg      480
acgaatgggg gcttggcgac gacagattcg gtgatgggga ggacggcagc ggcgaatcca      540
gaggcgggga gggctgcgac ggaggatctc gaggagggga gggctgcagc agcggatccg      600
gaggcgagga gggctacggc gacgacgggc gaggtgagt gcttcgacgg tggcggcggc       660
aggaggcttg gcaatggcgg attcggtggt gcggcgacga cgacgacgac gagtgagtgt      720
gagtgctccg gctgcggcag cgtcgatgac gatggtcgtt ga                         762
```

<210> SEQ ID NO 6
<211> LENGTH: 253
<212> TYPE: PRT
<213> ORGANISM: Oryza sativa

<400> SEQUENCE: 6

```
Met Val Gly Cys Glu His Met Val Leu Lys Val Val Leu Met Thr Ile
1               5                   10                  15

Lys Asp Arg Phe Ala Ser Tyr Cys Cys Tyr His Leu Ser Tyr Pro Val
            20                  25                  30

Ala Met Tyr Leu Gly Tyr Pro Pro Thr Arg Thr Ala Gly Tyr Tyr
        35                  40                  45

Tyr Ser Asp Ile Ser Thr Val Gly Pro Ala Ala Leu Leu Pro Tyr Val
    50                  55                  60

Glu Arg Leu Arg His Ser Gly Gly Gln Pro Ser Gly Glu Trp Asp Gly
65                  70                  75                  80

Leu Ile Pro Gly Glu Lys Tyr Ser Ser Gln Ile Arg Asp Gln Ser Ile
                85                  90                  95
```

| | | | | | | | | | | | |
|---|---|---|---|---|---|---|---|---|---|---|---|
|Leu|Gln|Asn|Leu|Ala|Asp|Glu|Leu|Val|Ser|Pro|Gly|Thr|Gly|Ser|Arg|
| | | |100| | | |105| | | |110| | | | |

Arg Glu Ala Arg Arg Phe Thr Pro Phe Thr Arg Ser His Cys Pro Leu
            115                 120                 125

Ser Leu Thr Ser Ser His Ser Ala Arg Ala Pro Pro Thr Val Ser
        130                 135                 140

Asp Asp Asp Gly Gly Leu Glu Arg Gln Gln Ala Ala Arg Ala Thr Thr
145                 150                 155                 160

Thr Asn Gly Gly Leu Ala Thr Thr Asp Ser Val Met Gly Arg Thr Ala
                165                 170                 175

Ala Ala Asn Pro Glu Ala Gly Arg Ala Ala Thr Glu Asp Leu Glu Glu
            180                 185                 190

Gly Arg Ala Ala Ala Asp Pro Glu Ala Arg Arg Ala Thr Ala Thr
        195                 200                 205

Thr Gly Glu Gly Glu Cys Phe Asp Gly Gly Gly Arg Arg Leu Gly
        210                 215                 220

Asn Gly Gly Phe Gly Gly Ala Ala Thr Thr Thr Thr Ser Glu Cys
225                 230                 235                 240

Glu Cys Ser Gly Cys Gly Ser Val Asp Asp Gly Arg
                245                 250

<210> SEQ ID NO 7
<211> LENGTH: 1454
<212> TYPE: DNA
<213> ORGANISM: Oryza sativa

<400> SEQUENCE: 7

```
ctgtccccct catctctctc ctcctcactc tcctcggctg ctctcctcct ctgtcggtgg      60
tgcactgctt gctcgatcct ctgcaatggc ggtcgacccg cgccaggtgg tggccggggtt    120
cctgaccctg tccatgttcg tcatgctcgg caacatgatc aagcacgacc acttcacccc    180
cgtcggcgcc ggccaggagg agttgggctt ggaggcaaca gcatagaat caaacgaaat     240
taaaattgca gatactactg aaatgactaa ggtcaacaag gctggagtgg atctcccaaa    300
ggagactgct gaggagatta gaccctgctg gtctaaacca agatcaaatg ttcaggagtc    360
taagggtttt gttacattct cattgactat gggccctgaa taccacatct cacagattac    420
tgatgctgtg gttatcgcaa gatatttagg tgcaacactt gtgcttccag aaattagagg    480
aaatgagtta ggaaagaggc ggaaattcga agacatgtat gatgtggata aattcatgac    540
gagcttggat ggagttgtca agtagtaca ttcacttcct aatgcagtgt cttctaagaa      600
gccagcagta gttagagtac caaaccgggt gactgaagag ttcatcacgg gaaccattga    660
gccgatcttc caagaaaata actacttacg acttgcgact attttctctt cagtaagttt    720
gaaacagaag gagtcgggta caaggacttt ggattcgact gcctgccttg caatgttcag    780
tggccttcag ttgaaacctg aattttcagc agtagccaag catatgttgg acaagcttaa    840
agaaataagc gagaaatccg atgggatggt tatagctatt gatttacaga ccgaattgct    900
agaaaagaag atctgtaaga cgaatggagg tgcaagaaga gaggctgtt attaccctca    960
ggaagttgtg cacttcctga agaaggttgg cttctctgct gatacaacca tctacttgac   1020
ggagacatgg tggcacaaaa gcctggatac tctgaaggag gcatttccaa acacttatac   1080
caaggatgat ataatgccgg ccgctaacaa aggcgagttc ctgaaatccg gggattcata   1140
ccttgcaaga gcactggacc tcaaaatctg ctcggagagc gacgtgttcg tccctgccat   1200
ccccggcctg ttctacggac atgtcgccgg taagaggatc gctgcaggcc tgacaaacat   1260
```

| | |
|---|---:|
| catagttcct gctccagtgt ccagcagttc agctctggct tcagagttcg tctccacata | 1320 |
| cgtgtccaag aagagccatc ttgcctactc atgttactgc tagtactgtt cttatatcat | 1380 |
| cagcatcagc atcagcatca ataagttcaa ctgaagtgag ttgcttggca agctttgggt | 1440 |
| acatatgtaa gtcc | 1454 |

<210> SEQ ID NO 8
<211> LENGTH: 1278
<212> TYPE: DNA
<213> ORGANISM: Oryza sativa

<400> SEQUENCE: 8

| | |
|---|---:|
| atggcggtcg acccgcgcca ggtggtggcc gggttcctga ccctgtccat gttcgtcatg | 60 |
| ctcggcaaca tgatcaagca cgaccacttc acccccgtcg cgccggcca ggaggagttg | 120 |
| ggcttggagg caacaggcat agaatcaaac gaaattaaaa ttgcagatac tactgaaatg | 180 |
| actaaggtca acaaggctgg agtggatctc ccaaaggaga ctgctgagga gattagaccc | 240 |
| tgctggtcta aaccaagatc aaatgttcag gagtctaagg gttttgttac attctcattg | 300 |
| actatgggcc ctgaatacca catctcacag attactgatg ctgtggttat cgcaagatat | 360 |
| ttaggtgcaa cacttgtgct tccagaaatt agaggaaatg agttaggaaa gaggcggaaa | 420 |
| ttcgaagaca tgtatgatgt ggataaattc atgacgagct ggatggagt tgtcaaagta | 480 |
| gtacattcac ttcctaatgc agtgtcttct aagaagccag cagtagttag agtaccaaac | 540 |
| cgggtgactg aagagttcat cacgggaacc attgagccga tcttccaaag aaataactac | 600 |
| ttacgacttg cgactatttt ctcttcagta agtttgaaac agaaggagtc gggtaacaag | 660 |
| gacttggatt cgactgcctg ccttgcaatg ttcagtggcc ttcagttgaa acctgaattt | 720 |
| tcagcagtag ccaagcatat gttggacaag cttaaagaaa taagcgagaa atccgatggg | 780 |
| atggttatag ctattgattt acagaccgaa ttgctagaaa agaagatctg taagacgaat | 840 |
| ggaggtgcaa gaagaagagg ctgttattac cctcaggaag ttgtgcactt cctgaagaag | 900 |
| gttggcttct ctgctgatac aaccatctac ttgacggaga catggtggca caaaagcctg | 960 |
| gatactctga aggaggcatt tccaaacact tataccaagg atgatataat gccggccgct | 1020 |
| aacaaaggcg agttcctgaa atccggggat tcataccttg caagagcact ggacctcaaa | 1080 |
| atctgctcgg agagcgacgt gttcgtccct gccatccccg gctgttcta cggacatgtc | 1140 |
| gccggtaaga ggatcgctgc aggcctgaca acatcatag ttcctgctcc agtgtccagc | 1200 |
| agttcagctc tggcttcaga gttcgtctcc acatacgtgt ccaagaagag ccatcttgcc | 1260 |
| tactcatgtt actgctag | 1278 |

<210> SEQ ID NO 9
<211> LENGTH: 425
<212> TYPE: PRT
<213> ORGANISM: Oryza sativa

<400> SEQUENCE: 9

```
Met Ala Val Asp Pro Arg Gln Val Val Ala Gly Phe Leu Thr Leu Ser
1               5                   10                  15

Met Phe Val Met Leu Gly Asn Met Ile Lys His Asp His Phe Thr Pro
            20                  25                  30

Val Gly Ala Gly Gln Glu Glu Leu Gly Leu Glu Ala Thr Gly Ile Glu
        35                  40                  45

Ser Asn Glu Ile Lys Ile Ala Asp Thr Thr Glu Met Thr Lys Val Asn
```

```
                  50                  55                  60
Lys Ala Gly Val Asp Leu Pro Lys Glu Thr Ala Glu Ile Arg Pro
 65                  70                  75                  80

Cys Trp Ser Lys Pro Arg Ser Asn Val Gln Glu Ser Lys Gly Phe Val
                 85                  90                  95

Thr Phe Ser Leu Thr Met Gly Pro Glu Tyr His Ile Ser Gln Ile Thr
                100                 105                 110

Asp Ala Val Val Ile Ala Arg Tyr Leu Gly Ala Thr Leu Val Leu Pro
                115                 120                 125

Glu Ile Arg Gly Asn Glu Leu Gly Lys Arg Lys Phe Glu Asp Met
130                 135                 140

Tyr Asp Val Asp Lys Phe Met Thr Ser Leu Asp Gly Val Val Lys Val
145                 150                 155                 160

Val His Ser Leu Pro Asn Ala Val Ser Ser Lys Lys Pro Ala Val Val
                165                 170                 175

Arg Val Pro Asn Arg Val Thr Glu Glu Phe Ile Thr Gly Thr Ile Glu
                180                 185                 190

Pro Ile Phe Gln Arg Asn Asn Tyr Leu Arg Leu Ala Thr Ile Phe Ser
                195                 200                 205

Ser Val Ser Leu Lys Gln Lys Glu Ser Gly Asn Lys Asp Leu Asp Ser
210                 215                 220

Thr Ala Cys Leu Ala Met Phe Ser Gly Leu Gln Leu Lys Pro Glu Phe
225                 230                 235                 240

Ser Ala Val Ala Lys His Met Leu Asp Lys Leu Lys Glu Ile Ser Glu
                245                 250                 255

Lys Ser Asp Gly Met Val Ile Ala Ile Asp Leu Gln Thr Glu Leu Leu
                260                 265                 270

Glu Lys Lys Ile Cys Lys Thr Asn Gly Gly Ala Arg Arg Gly Cys
                275                 280                 285

Tyr Tyr Pro Gln Glu Val His Phe Leu Lys Lys Val Gly Phe Ser
                290                 295                 300

Ala Asp Thr Thr Ile Tyr Leu Thr Glu Thr Trp Trp His Lys Ser Leu
305                 310                 315                 320

Asp Thr Leu Lys Glu Ala Phe Pro Asn Thr Tyr Lys Asp Asp Ile
                325                 330                 335

Met Pro Ala Ala Asn Lys Gly Glu Phe Leu Lys Ser Gly Asp Ser Tyr
                340                 345                 350

Leu Ala Arg Ala Leu Asp Leu Lys Ile Cys Ser Glu Ser Asp Val Phe
                355                 360                 365

Val Pro Ala Ile Pro Gly Leu Phe Tyr Gly His Val Ala Gly Lys Arg
                370                 375                 380

Ile Ala Ala Gly Leu Thr Asn Ile Ile Val Pro Ala Pro Val Ser Ser
385                 390                 395                 400

Ser Ser Ala Leu Ala Ser Glu Phe Val Ser Thr Tyr Val Ser Lys Lys
                405                 410                 415

Ser His Leu Ala Tyr Ser Cys Tyr Cys
                420                 425

<210> SEQ ID NO 10
<211> LENGTH: 231
<212> TYPE: DNA
<213> ORGANISM: Oryza sativa

<400> SEQUENCE: 10
```

| | |
|---|---|
| cgacgatgta catgaagaag cgccggcgcg cggaggcgga ggtggccctg gcgagaggct | 60 |
| ctggcgacaa ggtgttcggc aagaaggggt catgggacct caagtcgttc agggtccagg | 120 |
| cgttcgatga gcacaaggtg atcgacggcg tccgcgacaa gaacctcatt gacagcggca | 180 |
| tgtcaaggaa cgtgtaccaa ttttcccgga caaccctcat ctaatctccc g | 231 |

<210> SEQ ID NO 11
<211> LENGTH: 219
<212> TYPE: DNA
<213> ORGANISM: Oryza sativa

<400> SEQUENCE: 11

| | |
|---|---|
| atgtacatga agaagcgccg gcgcgcggag gcggaggtgg ccctggcgag aggctctggc | 60 |
| gacaaggtgt tcggcaagaa ggggtcatgg gacctcaagt cgttcagggt ccaggcgttc | 120 |
| gatgagcaca aggtgatcga cggcgtccgc gacaagaacc tcattgacag cggcatgtca | 180 |
| aggaacgtgt accaattttc cccgacaacc tcatctaa | 219 |

<210> SEQ ID NO 12
<211> LENGTH: 72
<212> TYPE: PRT
<213> ORGANISM: Oryza sativa

<400> SEQUENCE: 12

```
Met Tyr Met Lys Lys Arg Arg Arg Ala Glu Ala Glu Val Ala Leu Ala
1               5                   10                  15

Arg Gly Ser Gly Asp Lys Val Phe Gly Lys Lys Gly Ser Trp Asp Leu
            20                  25                  30

Lys Ser Phe Arg Val Gln Ala Phe Asp Glu His Lys Val Ile Asp Gly
        35                  40                  45

Val Arg Asp Lys Asn Leu Ile Asp Ser Gly Met Ser Arg Asn Val Tyr
    50                  55                  60

Gln Phe Ser Pro Thr Thr Leu Ile
65                  70
```

<210> SEQ ID NO 13
<211> LENGTH: 1176
<212> TYPE: DNA
<213> ORGANISM: Oryza sativa

<400> SEQUENCE: 13

| | |
|---|---|
| ctcttgtcat cccctccag cagtaacagc aacacgagaa gaattatcaa gtgaatgcag | 60 |
| ctcagtttct tcctctctga agacccttcc tacctatgct ctgttggcca tgccgttggg | 120 |
| gccattgtcg atgccggaaa accgacttg ctcgagttct cactgtggtc ggatgttggt | 180 |
| aaactcaccc ttgagcattg ccagctgctc agacaacgct tcatgtcatt ctctcactct | 240 |
| tgcccggttg ctttcaggtg gctcaccaat cttgccctgc gcaacctcgc gtttcaagaa | 300 |
| tcggacgtct cccatatcct aaacacatgc ataacctga gttccttgc cttgtgttct | 360 |
| tgtgtctcgg actttgttgt cctcaagatc gatgccccac actcggagct cctcacgctt | 420 |
| gaaattgtca cttgtggggtt tgacagagct gatctgatcc atttgccaaa tcttaggcgg | 480 |
| gtagtctgct gggattggtg ccttccaaac cccccaatcc gttttggcaa tgttactcgc | 540 |
| cttcacaaca tgagcctctc ttgctctgcg acgtatgacc agatgccgtt caggttgacc | 600 |
| gagcttatat caagcgccac aaaacttaact atccttatacc tggatttcca agatcagatg | 660 |
| atttggattg agccacaagg tcctaaactt ctctatcctg tattcagcaa cgtcagagat | 720 |

```
gtctatctttt gcaacatttt ctatgaatgt gacctgaact ggactgtgtt tgtccttgaa    780
gctgcagctc gtctcagcaa ctttatctc aagttatgtc agcatccatg tgaaaggaac    840
agatgcgagg acagcgctga aaggtcaat ttgttatggg atcagatgtc atctgatttc    900
aaacatcgcc acttgaatct attagagatt acaggatttg cgatggatga aagatgata    960 aattatacca ggcttattat ggagcgagct gtgaacttga agagaatccg cttgctcgat   1020
caagttccat gtgacaaggg caatgccatg aatggtatgg atctacatc ctcaaacaaa   1080 tggagatttc ctgttgacca aggagaaaag agtctaataa agcagaagct tatagatgga   1140
ttctcctcgt ctgctgaaat aaccatagga tgaatc                            1176

<210> SEQ ID NO 14
<211> LENGTH: 1119
<212> TYPE: DNA
<213> ORGANISM: Oryza sativa

<400> SEQUENCE: 14
atgcagctca gtttcttcct ctctgaagac ccttcctacc tatgctctgt tggccatgcc     60 gttgggcca ttgtcgatgc cggaaaaaacc gacttgctcg agttctcact gtggtcggat    120
gttggtaaac tcacccttga gcattgccag ctgctcagac aacgcttcat gtcattctct    180
cactcttgcc cggttgcttt caggtggctc accaatcttg ccctgcgcaa cctcgcgttt    240
caagaatcgg acgtctccca tcctaaaca acatgccata acctgaagtt ccttgccttg    300
tgttcttgtg tctcggactt tgttgtcctc aagatcgatg ccccacactc ggagctcctc    360
acgcttgaaa ttgtcacttg tgggtttgac agagctgatc tgatccattt gccaaatctt    420
aggcgggtag tctgctggga ttggtgccett ccaaaccccc caatccgtttt tggcaatgtt    480 actcgccttc acaacatgag cctctcttgc tctgcgacgt atgaccagat gccgttcagg    540
ttgaccgagc ttatatcaag cgccacaaac ttaactatct tatacctgga tttccaagat    600
cagatgattt ggattgagcc acaaggtcct aaacttctct atcctgtatt cagcaacgtc    660
agagatgtct atctttgcaa cattttctat gaatgtgacc tgaactggac tgtgtttgtc    720
cttgaagctg cagctcgtct cagcaacttt tatctcaagt tatgtcagca tccatgtgaa    780
aggaacagat gcgaggacag cgctgagaag gtcaatttgt tatgggatca gatgtcatct    840
gatttcaaac atcgccactt gaatctatta gagattacag gatttgcgat ggatgataag    900
atgataaatt ataccaggct tattatggag cgagctgtga acttgaagag aatccgcttg    960
ctcgatcaag ttccatgtga agggcaat gccatgaatg gtatgggatc tacatcctca   1020
aacaaatgga gatttcctgt tgaccaagga gaaagagtc taataaagca gaagcttata   1080
gatggattct cctcgtctgc tgaaataacc ataggatga                         1119

<210> SEQ ID NO 15
<211> LENGTH: 372
<212> TYPE: PRT
<213> ORGANISM: Oryza sativa

<400> SEQUENCE: 15

Met Gln Leu Ser Phe Phe Leu Ser Glu Asp Pro Ser Tyr Leu Cys Ser
1               5                   10                  15

Val Gly His Ala Val Gly Ala Ile Val Asp Ala Gly Lys Thr Asp Leu
                20                  25                  30

Leu Glu Phe Ser Leu Trp Ser Asp Val Gly Lys Leu Thr Leu Glu His
        35                  40                  45
```

Cys Gln Leu Leu Arg Gln Arg Phe Met Ser Phe Ser His Ser Cys Pro
 50                  55                  60
Val Ala Phe Arg Trp Leu Thr Asn Leu Ala Leu Arg Asn Leu Ala Phe
 65                  70                  75                  80
Gln Glu Ser Asp Val Ser His Ile Leu Asn Thr Cys His Asn Leu Lys
                 85                  90                  95
Phe Leu Ala Leu Cys Ser Cys Val Ser Asp Phe Val Leu Lys Ile
                100                 105                 110
Asp Ala Pro His Ser Glu Leu Leu Thr Leu Glu Ile Val Thr Cys Gly
                115                 120                 125
Phe Asp Arg Ala Asp Leu Ile His Leu Pro Asn Leu Arg Arg Val Val
130                 135                 140
Cys Trp Asp Trp Cys Leu Pro Asn Pro Pro Ile Arg Phe Gly Asn Val
145                 150                 155                 160
Thr Arg Leu His Asn Met Ser Leu Ser Cys Ser Ala Thr Tyr Asp Gln
                165                 170                 175
Met Pro Phe Arg Leu Thr Glu Leu Ile Ser Ser Ala Thr Asn Leu Thr
                180                 185                 190
Ile Leu Tyr Leu Asp Phe Gln Asp Gln Met Ile Trp Ile Glu Pro Gln
                195                 200                 205
Gly Pro Lys Leu Leu Tyr Pro Val Phe Ser Asn Val Arg Asp Val Tyr
210                 215                 220
Leu Cys Asn Ile Phe Tyr Glu Cys Asp Leu Asn Trp Thr Val Phe Val
225                 230                 235                 240
Leu Glu Ala Ala Ala Arg Leu Ser Asn Phe Tyr Leu Lys Leu Cys Gln
                245                 250                 255
His Pro Cys Glu Arg Asn Arg Cys Glu Asp Ser Ala Glu Lys Val Asn
                260                 265                 270
Leu Leu Trp Asp Gln Met Ser Ser Asp Phe Lys His Arg His Leu Asn
                275                 280                 285
Leu Leu Glu Ile Thr Gly Phe Ala Met Asp Asp Lys Met Ile Asn Tyr
                290                 295                 300
Thr Arg Leu Ile Met Glu Arg Ala Val Asn Leu Lys Arg Ile Arg Leu
305                 310                 315                 320
Leu Asp Gln Val Pro Cys Asp Lys Gly Asn Ala Met Asn Gly Met Gly
                325                 330                 335
Ser Thr Ser Ser Asn Lys Trp Arg Phe Pro Val Asp Gln Gly Glu Lys
                340                 345                 350
Ser Leu Ile Lys Gln Lys Leu Ile Asp Gly Phe Ser Ser Ser Ala Glu
                355                 360                 365
Ile Thr Ile Gly
    370

<210> SEQ ID NO 16
<211> LENGTH: 285
<212> TYPE: DNA
<213> ORGANISM: Oryza sativa

<400> SEQUENCE: 16
atgtcgcctc tcctcccctg cacatggatt cagtgggccg ggccctcccc ctccacgtgg     60
atcctgccac tcttccgcc ccttcatcgc gcatggatcc ggcgttgcgc atcgacggcg    120
aggaggagaa acaatgacta cggcaacggt ggccggagga gcttgctgga ttttctggcg    180
gcagcgacag gagggggcgat gggagacatg gagaccggga atggcatcgg cggtggcaat    240
gatgatgatc gttgtcacac cctgaagttc tcctcccaag cctaa 285

<210> SEQ ID NO 17
<211> LENGTH: 285
<212> TYPE: DNA
<213> ORGANISM: Oryza sativa

<400> SEQUENCE: 17
atgtcgcctc tcctcccctg cacatggatt cagtgggccg ggccctcccc ctccacgtgg    60
atcctgccac ctcttccgcc ccttcatcgc gcatggatcc ggcgttgcgc atcgacggcg   120
aggaggagaa acaatgacta cggcaacggt ggccgggaga gcttgctgga ttttctggcg   180
gcagcgacag gagggcgat gggagacatg gagaccggga atggcatcgg cggtggcaat   240
gatgatgatc gttgtcacac cctgaagttc tcctcccaag cctaa                  285

<210> SEQ ID NO 18
<211> LENGTH: 94
<212> TYPE: PRT
<213> ORGANISM: Oryza sativa

<400> SEQUENCE: 18

Met Ser Pro Leu Leu Pro Cys Thr Trp Ile Gln Trp Ala Gly Pro Ser
1               5                   10                  15

Pro Ser Thr Trp Ile Leu Pro Pro Leu Pro Pro Leu His Arg Ala Trp
            20                  25                  30

Ile Arg Arg Cys Ala Ser Thr Ala Arg Arg Arg Asn Asn Asp Tyr Gly
        35                  40                  45

Asn Gly Gly Arg Glu Ser Leu Leu Asp Phe Leu Ala Ala Ala Thr Gly
    50                  55                  60

Gly Ala Met Gly Asp Met Glu Thr Gly Asn Gly Ile Gly Gly Gly Asn
65                  70                  75                  80

Asp Asp Asp Arg Cys His Thr Leu Lys Phe Ser Ser Gln Ala
                85                  90

<210> SEQ ID NO 19
<211> LENGTH: 560
<212> TYPE: DNA
<213> ORGANISM: Oryza sativa

<400> SEQUENCE: 19
ctagaggagg cgaggtggtg gaggagccgg cgaatctgcg atgaccccgc ggtggcgacg    60
gccccacgac ggcgacgggc tcaccagatc cagggccggc gacgaccccg cgatgccaac   120
gggcggaggg agagcggtgg cggcgcggca ctcaagatcc aacctccgcg tgccgctcgc   180
cgtggtggag gagctgttgg ccaccctgcg caccatcggc ggcccacga agatccgcga   240 cagcgacgac ctcacggcag ccgacgacgg gagagagagg ccgatgggag agagaggcca   300
ccccgcgctc ccctcgcggt cgtccacccc gcgcgctgct cgcctttcgc caccgtgcac   360
cgttcgccat ctatggagga gacgagaaga ggagaggaag agacaaggac ggcagcgtcg   420
gtgggctgat gagccctttta gctgggctat agaagggtac tttcataatt tttcactttg   480
tgggctggag tatctttatc aagtggtctc agattttgaa gaacccattg gaggtatcct   540
tcagtgagag atgagttccc                                              560

<210> SEQ ID NO 20
<211> LENGTH: 507
<212> TYPE: DNA
<213> ORGANISM: Oryza sativa

<400> SEQUENCE: 20

```
atgaccccgc ggtggcgacg gccccacgac ggcgacgggc tcaccagatc cagggccggc      60
gacgaccccg cgatgccaac gggcggaggg agagcggtgg cggcgcggca ctcaagatcc     120
aacctccgcg tgccgctcgc cgtggtggag gagctgttgg ccaccctgcg caccatcggc     180
ggccccacga agatccgcga cagcgacgac ctcacggcag ccgacgacgg gagagagagg     240
ccgatgggag agagaggcca ccccgcgctc ccctcgcggt cgtccacccc gcgcgctgct     300
cgcctttcgc caccgtgcac cgttcgccat ctatggagga gacgagaaga ggagaggaag     360
agacaaggac ggcagcgtcg gtgggctgat gagccctta gctgggctat agaagggtac      420
tttcataatt tttcactttg tgggctggag tatctttatc aagtggtctc agattttgaa     480
gaacccattg gaggtatcct tcagtga                                         507
```

<210> SEQ ID NO 21
<211> LENGTH: 168
<212> TYPE: PRT
<213> ORGANISM: Oryza sativa

<400> SEQUENCE: 21

```
Met Thr Pro Arg Trp Arg Arg Pro His Asp Gly Asp Gly Leu Thr Arg
1               5                   10                  15
Ser Arg Ala Gly Asp Asp Pro Ala Met Pro Thr Gly Gly Gly Arg Ala
            20                  25                  30
Val Ala Ala Arg His Ser Arg Ser Asn Leu Arg Val Pro Leu Ala Val
        35                  40                  45
Val Glu Glu Leu Leu Ala Thr Leu Arg Thr Ile Gly Gly Pro Thr Lys
    50                  55                  60
Ile Arg Asp Ser Asp Asp Leu Thr Ala Ala Asp Asp Gly Arg Glu Arg
65                  70                  75                  80
Pro Met Gly Glu Arg Gly His Pro Ala Leu Pro Ser Arg Ser Ser Thr
                85                  90                  95
Pro Arg Ala Ala Arg Leu Ser Pro Pro Cys Thr Val Arg His Leu Trp
            100                 105                 110
Arg Arg Arg Glu Glu Glu Arg Lys Arg Gln Gly Arg Gln Arg Arg Trp
        115                 120                 125
Ala Asp Glu Pro Phe Ser Trp Ala Ile Glu Gly Tyr Phe His Asn Phe
    130                 135                 140
Ser Leu Cys Gly Leu Glu Tyr Leu Tyr Gln Val Val Ser Asp Phe Glu
145                 150                 155                 160
Glu Pro Ile Gly Gly Ile Leu Gln
                165
```

<210> SEQ ID NO 22
<211> LENGTH: 2421
<212> TYPE: DNA
<213> ORGANISM: Oryza sativa

<400> SEQUENCE: 22

```
cacagacaca gtggaagcaa aatctccatg gcggcggcgg cggcggcagc agcagcagaa      60
gacgaggaga agaggcctct gctgcttcgt ccgaacggcg gcggcggcaa ggaggaggag     120
gacaagggcg gcggcggtgg ggtggagggcg tgcgtgctga tactggggac ggagctgagc     180
gactgcctgg cgttcgccgg catcgcgagg aacctggtga gctacctcac cggcgtggta     240
ggggagagca atgtcgccgc cgccagggac gtgtcggcgt ggacgggcac ctgcttcctc     300
```

```
acgccgctcg tcggcgcatt catcgccgac tccttcttgg gtcgccgcac caccatcctc    360
ctcttcctct ccatctactc catggtatac tttttttatt attaagaaaa gtatgctcaa    420
acaagttttt tgttaatgcg aaaaactgaa tgtttgaaga gattttctt agttttaat     480 gtgaaaatat atcatactcc tttattcaat tttcattatt cagacatttt tgtgaatgaa    540
atgtttttac aacaagattt agataacaaa caaaagcata tcaaatatga caatagagaa    600
tttcggaatt aaaggtcaag caaagcttaa gaagattttt tttgggcaaa ttttttatg     660 gtcttcatgc tttacaggga ctgaaaaaga gagagaacaa taaatttctt atggcaatca    720
agaatttctg cgaaatgtca agcaaaaatt aagaagatat tatgtttttt tttcacaagt    780
tctttagaaa agaacatctt cttatggcaa tcaagaattt cttaaaggtc aatcaaaatt    840
taagatttaa ttttgtttc acaaattatt ttgatggtct tcaccagtgg actgaaaaaa     900
caataaagaa cgaaaaattt ctgaaatttc gttataaaat ttcaatctgt gacaggggat    960
gatcacgctc acagtctcgg cgtcgttcgc aacccacac cttgatgcat cctccgatgg     1020
cgtcctccgc gccaccgtgt tcctggggct ctacctcgtc gccctcggcg tcggtggcat    1080
caagccgtgc gcctcgccgc tgggcgccga ccagttcgac gacgacgacg cggcgccggc    1140
ggcgagggcg tccttcttca actggtacta cttctgcatc aacgtcggct cgctgctggc    1200
ggccaccgtg cttgtgtggg tgcaggagcg cgccggctgg tggctcggct cgccatccc     1260 ggcggcggtc atgaccgccg cgctcgccgc cttcctcttc tgctccaccc tgtgcggcct    1320 ccggcgttc cacacgccgc cggggagccc cctcacgcgg ctctgccagg tggtcgtcgc     1380
cgccgtcagg aatcgcggcg tggagcttcc cggcgacagc tcgctcctgc atcagctccc    1440
cgacggcgac taccggatca tcgagcacac caatcagttc gcgttcctgg acaaggcggc    1500
cgtagtggcg tcgccgccgg cggtggcgat ggcgagcccg tggatgctgt gcacggtgac    1560
gcaggtggag gaggtcaaga tgctgctgcg gctgtccacc gtgtggccga cggtggtgtt    1620
cttcttcgcc gccacggcgc agatgtcgtc gacgttcgtg gagcagggga aggcgatgga    1680
cacccgcgtc ggcccgctcg acgtgccgcc ggcgacgctg tccaccttcg aggtggtcag    1740
catcctcctc tgcgtcccgg cctacgacgc gcgctgatg ccgctcgccc gccgcgtcac     1800
cggcgaccgc cgcggcctgt cgcagctgca gcggctcggc gtcgggctgg cgctgtcggc    1860
gctggccatg gcgtactcgg cgctgctcga ggcgagccgc cggcggcgcg cggcgacgag    1920
catcgtgtgg caggcgccgt cgtacatggc gctgggcgcg cggaggtgt tcaccagcgt    1980 cggcctgctc gagttcttct acgaccaggc gcccgacacc ataaagagcc tgtgcaccgc    2040
ggtgagcctc gtcgccgtgg cggccggaag ctacctcaac tcggccatcg tcgcggtggt    2100
cgcgtgggcg acggcgccgg agaagggcgg cggcggcggg tggattcccg acgatctcaa    2160
tcgaggacgg ctggattgct tcttctggct catgttcggc ctcagctgtg taaacctgct    2220
ggcgttcgtt tactcttcta cgagatacag ctacagggtt gctaactaat acttcctctg    2280
tttcacaacg taagtcattc aatcatttcc tatattcata ttgatgttga tgaatctaga    2340
taaatatata tgtctagatt cgttaacatc aatataaatg tggaaaatgc tagaatgact    2400
tatattgtga aacggaggga g                                              2421
```

<210> SEQ ID NO 23
<211> LENGTH: 1671
<212> TYPE: DNA
<213> ORGANISM: Oryza sativa

<400> SEQUENCE: 23

```
atggcggcgg cggcggcggc agcagcagca gaagacgagg agaagaggcc tctgctgctt      60
cgtccgaacg gcggcggcgg caaggaggag gaggacaagg gcggcggcgg tgggtggagg     120
gcgtgcgtgc tgatactggg gacggagctg agcgactgcc tggcgttcgc cggcatcgcg     180
aggaacctgg tgagctacct caccggcgtg gtaggggaga gcaatgtcgc cgccgccagg     240
gacgtgtcgg cgtggacggg cacctgcttc ctcacgccgc tcgtcggcgc attcatcgcc     300
gactccttct gggtcgccg caccaccatc ctcctcttcc tctccatcta ctccatgggg     360
atgatcacgc tcacagtctc ggcgtcgttc gcaaccccac accttgatgc atcctccgat     420
ggcgtcctcc gcgccaccgt gttcctgggg ctctacctcg tcgccctcgg cgtcggtggc     480
atcaagccgt gcgcctcgcc gctgggcgcc gaccagttcg acgacgacga cgcggcgccg     540
gcggcgaggg cgtccttctt caactggtac tacttctgca tcaacgtcgg ctcgctgctg     600
gcggccaccg tgcttgtgtg ggtgcaggag cgcgccggct ggtggctcgg cttcgccatc     660
ccggcggcgg tcatgaccgc cgcgctcgcc gccttcctct tctgctccac cctgtgcggc     720
ctccgggcgt tccacacgcc gccggggagc cccctcacgc ggctctgcca ggtggtcgtc     780
gccgccgtca ggaatcgcgg cgtggagctt cccggcgaca gctcgctcct gcatcagctc     840
cccgacggcg actaccggat catcgagcac accaatcagt tcgcgttcct ggacaaggcg     900
gccgtagtgg cgtcgccgcc ggcggtggcg atggcgagcc gtggatgct gtgcacggtg     960
acgcaggtgg aggaggtcaa gatgctgctg cggctgtcca ccgtgtggcc gacggtggtg    1020
ttcttcttcg ccgccacggc gcagatgtcg tcgacgttcg tggagcaggg gaaggcgatg    1080
gacaccccgcg tcggccgcgct cgacgtgccg ccggcgacgc tgtccacctt cgaggtggtc    1140
agcatcctcc tctgcgtccc ggcctacgac gccgcgctga tgccgctcgc ccgccgcgtc    1200
accggcgacc gccgcggcct gtcgcagctg cagcggctcg gcgtcgggct ggcgctgtcg    1260
gcgctggcca tggcgtactc ggcgctgctc gaggcgagcc gccggcggcg cgcggcgacg    1320
agcatcgtgt ggcaggcgcc gtcgtacatg gcgctgggcg cggcggaggt gttcaccagc    1380
gtcggcctgc tcgagttctt ctacgaccag gcgcccgaca ccataaagag cctgtgcacc    1440
gcggtgagcc tcgtcgccgt ggcggccgga agctacctca actcggccat cgtcgcggtg    1500
gtcgcgtggg cgacggcgcc ggagaagggc ggcggcggcg ggtggattcc cgacgatctc    1560
aatcgaggac ggctggattg cttcttctgg ctcatgttcg gcctcagctg tgtaaacctg    1620
ctggcgttcg tttactcttc tacgagatac agctacaggg ttgctaacta a             1671
```

<210> SEQ ID NO 24
<211> LENGTH: 556
<212> TYPE: PRT
<213> ORGANISM: Oryza sativa

<400> SEQUENCE: 24

```
Met Ala Ala Ala Ala Ala Ala Ala Glu Asp Glu Glu Lys Arg
1               5                   10                  15

Pro Leu Leu Arg Pro Asn Gly Gly Gly Lys Glu Glu Asp
            20                  25                  30

Lys Gly Gly Gly Gly Trp Arg Ala Cys Val Leu Ile Leu Gly Thr
        35                  40                  45

Glu Leu Ser Asp Cys Leu Ala Phe Ala Gly Ile Ala Arg Asn Leu Val
    50                  55                  60

Ser Tyr Leu Thr Gly Val Val Gly Glu Ser Asn Val Ala Ala Ala Arg
```

```
            65                  70                  75                  80
Asp Val Ser Ala Trp Thr Gly Thr Cys Phe Leu Thr Pro Leu Val Gly
                    85                  90                  95

Ala Phe Ile Ala Asp Ser Phe Leu Gly Arg Arg Thr Thr Ile Leu Leu
                100                 105                 110

Phe Leu Ser Ile Tyr Ser Met Gly Met Ile Thr Leu Thr Val Ser Ala
            115                 120                 125

Ser Phe Ala Thr Pro His Leu Asp Ala Ser Ser Asp Gly Val Leu Arg
        130                 135                 140

Ala Thr Val Phe Leu Gly Leu Tyr Leu Val Ala Leu Gly Val Gly Gly
145                 150                 155                 160

Ile Lys Pro Cys Ala Ser Pro Leu Gly Ala Asp Gln Phe Asp Asp Asp
                165                 170                 175

Asp Ala Ala Pro Ala Ala Arg Ala Ser Phe Phe Asn Trp Tyr Tyr Phe
                180                 185                 190

Cys Ile Asn Val Gly Ser Leu Leu Ala Ala Thr Val Leu Val Trp Val
            195                 200                 205

Gln Glu Arg Ala Gly Trp Trp Leu Gly Phe Ala Ile Pro Ala Ala Val
        210                 215                 220

Met Thr Ala Ala Leu Ala Ala Phe Leu Phe Cys Ser Thr Leu Cys Gly
225                 230                 235                 240

Leu Arg Ala Phe His Thr Pro Pro Gly Ser Pro Leu Thr Arg Leu Cys
                245                 250                 255

Gln Val Val Val Ala Ala Val Arg Asn Arg Gly Val Glu Leu Pro Gly
            260                 265                 270

Asp Ser Ser Leu Leu His Gln Leu Pro Asp Gly Asp Tyr Arg Ile Ile
        275                 280                 285

Glu His Thr Asn Gln Phe Ala Phe Leu Asp Lys Ala Ala Val Val Ala
        290                 295                 300

Ser Pro Pro Ala Val Ala Met Ala Ser Pro Trp Met Leu Cys Thr Val
305                 310                 315                 320

Thr Gln Val Glu Glu Val Lys Met Leu Leu Arg Leu Ser Thr Val Trp
                325                 330                 335

Pro Thr Val Val Phe Phe Ala Ala Thr Ala Gln Met Ser Ser Thr
                340                 345                 350

Phe Val Glu Gln Gly Lys Ala Met Asp Thr Arg Val Gly Pro Leu Asp
            355                 360                 365

Val Pro Pro Ala Thr Leu Ser Thr Phe Glu Val Val Ser Ile Leu Leu
370                 375                 380

Cys Val Pro Ala Tyr Asp Ala Ala Leu Met Pro Leu Ala Arg Arg Val
385                 390                 395                 400

Thr Gly Asp Arg Arg Gly Leu Ser Gln Leu Gln Arg Leu Gly Val Gly
                405                 410                 415

Leu Ala Leu Ser Ala Leu Ala Met Ala Tyr Ser Ala Leu Leu Glu Ala
            420                 425                 430

Ser Arg Arg Arg Arg Ala Ala Thr Ser Ile Val Trp Gln Ala Pro Ser
        435                 440                 445

Tyr Met Ala Leu Gly Ala Ala Glu Val Phe Thr Ser Val Gly Leu Leu
        450                 455                 460

Glu Phe Phe Tyr Asp Gln Ala Pro Asp Thr Ile Lys Ser Leu Cys Thr
465                 470                 475                 480

Ala Val Ser Leu Val Ala Val Ala Ala Gly Ser Tyr Leu Asn Ser Ala
                485                 490                 495
```

```
Ile Val Ala Val Val Ala Trp Ala Thr Ala Pro Glu Lys Gly Gly Gly
            500                 505                 510

Gly Gly Trp Ile Pro Asp Asp Leu Asn Arg Gly Arg Leu Asp Cys Phe
        515                 520                 525

Phe Trp Leu Met Phe Gly Leu Ser Cys Val Asn Leu Leu Ala Phe Val
530                 535                 540

Tyr Ser Ser Thr Arg Tyr Ser Tyr Arg Val Ala Asn
545                 550                 555
```

<210> SEQ ID NO 25
<211> LENGTH: 31
<212> TYPE: DNA
<213> ORGANISM: Artificial Sequence
<220> FEATURE:
<223> OTHER INFORMATION: Forward primer for cloning gDNA of OsLNTP12 gene

<400> SEQUENCE: 25
ctgctgaggc gaagagagga gatcggcgag g           31

<210> SEQ ID NO 26
<211> LENGTH: 32
<212> TYPE: DNA
<213> ORGANISM: Artificial Sequence
<220> FEATURE:
<223> OTHER INFORMATION: Reverse primer for cloning gDNA of OsLNTP12 gene

<400> SEQUENCE: 26
ccgctgaggc aacacatatg gctccgctga tg          32

<210> SEQ ID NO 27
<211> LENGTH: 34
<212> TYPE: DNA
<213> ORGANISM: Artificial Sequence
<220> FEATURE:
<223> OTHER INFORMATION: Forward primer for cloning gDNA of OsLNTP13 gene

<400> SEQUENCE: 27
ctgctgagga ttaaaacttg acaatggtgg gttg        34

<210> SEQ ID NO 28
<211> LENGTH: 33
<212> TYPE: DNA
<213> ORGANISM: Artificial Sequence
<220> FEATURE:
<223> OTHER INFORMATION: Reverse primer for cloning gDNA of OsLNTP13 gene

<400> SEQUENCE: 28
ccgctgagga gagatgggat ggacgtcgtt tgc         33

<210> SEQ ID NO 29
<211> LENGTH: 26
<212> TYPE: DNA
<213> ORGANISM: Artificial Sequence
<220> FEATURE:
<223> OTHER INFORMATION: Forward primer for cloning cDNA of OsGRRP1 gene

<400> SEQUENCE: 29
ctgtccccct catctctctc ctcctc                26

<210> SEQ ID NO 30

-continued

```
<211> LENGTH: 29
<212> TYPE: DNA
<213> ORGANISM: Artificial Sequence
<220> FEATURE:
<223> OTHER INFORMATION: Reverse primer for cloning cDNA of OsGRRP1 gene

<400> SEQUENCE: 30
ggacttacat atgtacccaa agcttgccc                                    29

<210> SEQ ID NO 31
<211> LENGTH: 23
<212> TYPE: DNA
<213> ORGANISM: Artificial Sequence
<220> FEATURE:
<223> OTHER INFORMATION: Forward primer for cloning cDNA of OsLNTP14
      gene

<400> SEQUENCE: 31
cgacgatgta catgaagaag cgc                                          23

<210> SEQ ID NO 32
<211> LENGTH: 24
<212> TYPE: DNA
<213> ORGANISM: Artificial Sequence
<220> FEATURE:
<223> OTHER INFORMATION: Reverse primer for cloning cDNA of OsLNTP14
      gene

<400> SEQUENCE: 32
cgggagatta gatgagggtt gtcg                                         24

<210> SEQ ID NO 33
<211> LENGTH: 27
<212> TYPE: DNA
<213> ORGANISM: Artificial Sequence
<220> FEATURE:
<223> OTHER INFORMATION: Forward primer for cloning cDNA of OsLNTP15
      gene

<400> SEQUENCE: 33
ctcttgtcat cccctccag cagtaac                                       27

<210> SEQ ID NO 34
<211> LENGTH: 29
<212> TYPE: DNA
<213> ORGANISM: Artificial Sequence
<220> FEATURE:
<223> OTHER INFORMATION: Reverse primer for cloning cDNA of OsLNTP15
      gene

<400> SEQUENCE: 34
gattcatcct atggttattt cagcagacg                                    29

<210> SEQ ID NO 35
<211> LENGTH: 30
<212> TYPE: DNA
<213> ORGANISM: Artificial Sequence
<220> FEATURE:
<223> OTHER INFORMATION: Forward primer for cloning gDNA of OsLNTP16
      gene

<400> SEQUENCE: 35
ctgctgagga tgtcgcctct cctcccctgc                                   30

<210> SEQ ID NO 36
<211> LENGTH: 33
<212> TYPE: DNA
```

```
<213> ORGANISM: Artificial Sequence
<220> FEATURE:
<223> OTHER INFORMATION: Reverse primer for cloning gDNA of OsLNTP16
      gene

<400> SEQUENCE: 36
ccgctgaggt taggcttggg aggagaactt cag                                33

<210> SEQ ID NO 37
<211> LENGTH: 23
<212> TYPE: DNA
<213> ORGANISM: Artificial Sequence
<220> FEATURE:
<223> OTHER INFORMATION: Forward primer for cloning gDNA of OsLNTP17
      gene

<400> SEQUENCE: 37
ctagaggagg cgaggtggtg gag                                           23

<210> SEQ ID NO 38
<211> LENGTH: 27
<212> TYPE: DNA
<213> ORGANISM: Artificial Sequence
<220> FEATURE:
<223> OTHER INFORMATION: Reverse primer for cloning gDNA of OsLNTP17
      gene

<400> SEQUENCE: 38
gggaactcat ctctcactga aggatac                                       27

<210> SEQ ID NO 39
<211> LENGTH: 27
<212> TYPE: DNA
<213> ORGANISM: Artificial Sequence
<220> FEATURE:
<223> OTHER INFORMATION: Forward primer for cloning gDNA of OsPTR11 gene

<400> SEQUENCE: 39
cacagacaca gtggaagcaa aatctcc                                       27

<210> SEQ ID NO 40
<211> LENGTH: 33
<212> TYPE: DNA
<213> ORGANISM: Artificial Sequence
<220> FEATURE:
<223> OTHER INFORMATION: Reverse primer for cloning gDNA of OsPTR11 gene

<400> SEQUENCE: 40
ctccctccgt ttcacaatat aagtcattct agc                                33

<210> SEQ ID NO 41
<211> LENGTH: 18
<212> TYPE: DNA
<213> ORGANISM: Artificial Sequence
<220> FEATURE:
<223> OTHER INFORMATION: Forward primer for real-time PCR analysis of
      OsLNTP12 gene

<400> SEQUENCE: 41
atgcagtagc gttgggtg                                                 18

<210> SEQ ID NO 42
<211> LENGTH: 20
<212> TYPE: DNA
<213> ORGANISM: Artificial Sequence
<220> FEATURE:
<223> OTHER INFORMATION: Reverse primer for real-time PCR analysis of
```

OsLNTP12 gene

<400> SEQUENCE: 42
atctgcatct catccgcatc                                                     20

<210> SEQ ID NO 43
<211> LENGTH: 23
<212> TYPE: DNA
<213> ORGANISM: Artificial Sequence
<220> FEATURE:
<223> OTHER INFORMATION: Forward primer for real-time PCR analysis of
      OsLNTP15 gene

<400> SEQUENCE: 43
gtcatctgat ttcaaacatc gcc                                                 23

<210> SEQ ID NO 44
<211> LENGTH: 21
<212> TYPE: DNA
<213> ORGANISM: Artificial Sequence
<220> FEATURE:
<223> OTHER INFORMATION: Reverse primer for real-time PCR analysis of
      OsLNTP15 gene

<400> SEQUENCE: 44
tcacatggaa cttgatcgag c                                                   21

<210> SEQ ID NO 45
<211> LENGTH: 18
<212> TYPE: DNA
<213> ORGANISM: Artificial Sequence
<220> FEATURE:
<223> OTHER INFORMATION: Forward primer for real-time PCR analysis of
      OsPTR11 gene

<400> SEQUENCE: 45
ttctggctca tgttcggc                                                       18

<210> SEQ ID NO 46
<211> LENGTH: 22
<212> TYPE: DNA
<213> ORGANISM: Artificial Sequence
<220> FEATURE:
<223> OTHER INFORMATION: Reverse primer for real-time PCR analysis of
      OsPTR11 gene

<400> SEQUENCE: 46
accctgtagc tgtatctcgt ag                                                  22

<210> SEQ ID NO 47
<211> LENGTH: 315
<212> TYPE: DNA
<213> ORGANISM: Oryza sativa

<400> SEQUENCE: 47
atgtcgcgcc gtcctgtcca ccgccgccgc gtccgcctcc ccatcaccca ccgcgtcgtc        60
cttcgcctcg ccgatatcct ctctccgcgc tgccatcaat ctcgcgacgg ccaccgtcgc       120
tgccatgcag ccgtcgtcgt cagatcctcc tccactgccc caacgccggt tgtgtcgtcc       180
tgtccgccaa cacctgcgca ccctccgtcg cttgatattc ctgcgagttt tattaagaaa       240
attacttttt tcctgctgtt gttacacttg ctgtgtggag agaaaacttt gtcagaagct       300
aaatattgtt gttaa                                                        315

```
<210> SEQ ID NO 48
<211> LENGTH: 104
<212> TYPE: PRT
<213> ORGANISM: Oryza sativa

<400> SEQUENCE: 48

Met Ser Arg Arg Pro Val His Arg Arg Val Arg Leu Pro Ile Thr
1               5                   10                  15

His Arg Val Val Leu Arg Leu Ala Asp Ile Leu Ser Pro Arg Cys His
            20                  25                  30

Gln Ser Arg Asp Gly His Arg Arg Cys His Ala Ala Val Val Val Arg
        35                  40                  45

Ser Ser Ser Thr Ala Pro Thr Pro Val Val Ser Cys Pro Pro Thr
    50                  55                  60

Pro Ala His Pro Pro Ser Leu Asp Ile Pro Ala Ser Phe Ile Lys Lys
65                  70                  75                  80

Ile Thr Phe Phe Leu Leu Leu His Leu Leu Cys Gly Glu Lys Thr
                85                  90                  95

Leu Ser Glu Ala Lys Tyr Cys Cys
            100

<210> SEQ ID NO 49
<211> LENGTH: 606
<212> TYPE: DNA
<213> ORGANISM: Oryza sativa

<400> SEQUENCE: 49
atgggatggg acgaacccac ttttaaaggt gtttggttta ggggtgagtg ggatgggttg      60
gttcctggac aggaatattc ctctcagatc cggaaccaag ccatccggaa aaatctcgtg    120
gacgagctcg tcccacctgg gacgagcgca cggcgtgagg cgcgccgctt cgccacgctc    180
gttcgctcgc accgtcgcac gccactcgct cgcccctctc actcgcatct tgctcctcca    240
cccatcgtga gtgatgacga tggcggcaga tccggtggtg gggagggtgg cggcagtgaa    300
tctgaaggca gggagggcgg ggagggctcg tcatcggtgg cgaatccgga ggcggggatg    360
gcggcggtgg cgaatccgga ggcggggagg cggtggtag cgaatctggt agcgaggagg    420
gctgcggcgg tgtggagggc tccgatggcg gcgacagtga tggcgggcaa gggtgagtgc    480
tccggccacc acttccgcat cgtcgttgcc tctgactcgc tcctccttcc gcccgcgccg    540
atggtagccg ctcctccttc cgcccgcgcc gccggtcgcc cctcctcatt ccgcctgcgc    600
cactag                                                                 606

<210> SEQ ID NO 50
<211> LENGTH: 201
<212> TYPE: PRT
<213> ORGANISM: Oryza sativa

<400> SEQUENCE: 50

Met Gly Trp Asp Glu Pro Thr Phe Lys Gly Val Trp Phe Arg Gly Glu
1               5                   10                  15

Trp Asp Gly Leu Val Pro Gly Gln Glu Tyr Ser Ser Gln Ile Arg Asn
            20                  25                  30

Gln Ala Ile Arg Lys Asn Leu Val Asp Glu Leu Val Pro Pro Gly Thr
        35                  40                  45

Ser Ala Arg Arg Glu Ala Arg Arg Phe Ala Thr Leu Val Arg Ser His
    50                  55                  60

Arg Arg Thr Pro Leu Ala Arg Pro Ser His Ser His Leu Ala Pro Pro
```

```
                65                  70                  75                  80
Pro Ile Val Ser Asp Asp Gly Gly Arg Ser Gly Gly Glu Gly
                    85                  90                  95
Gly Gly Ser Glu Ser Glu Gly Arg Glu Gly Gly Glu Gly Ser Ser Ser
                100                 105                 110
Val Ala Asn Pro Glu Ala Gly Met Ala Ala Val Ala Asn Pro Glu Ala
                115                 120                 125
Gly Arg Ala Val Val Ala Asn Leu Val Ala Arg Ala Ala Ala Val
        130                 135                 140
Trp Arg Ala Pro Met Ala Ala Thr Val Met Ala Gly Lys Gly Glu Cys
145                 150                 155                 160
Ser Gly His His Phe Arg Ile Val Val Ala Ser Asp Ser Leu Leu Leu
                    165                 170                 175
Pro Pro Ala Pro Met Val Ala Ala Pro Pro Ser Ala Arg Ala Ala Gly
                180                 185                 190
Arg Pro Ser Ser Phe Arg Leu Arg His
                195                 200

<210> SEQ ID NO 51
<211> LENGTH: 1266
<212> TYPE: DNA
<213> ORGANISM: Zea mays

<400> SEQUENCE: 51
atggcggtcg acccgcggca ggtcgtggcg ggcttcctca ccctctccat gttcgtcatg      60
ctgggcaaca tgatcaagca cgaccacttc tctcccgtca ccgaggagat gggcttgaag     120
gcaacaggtg cgcgatccaa cacaatgaag cttgataaca atgctgaaat gaacagtgtc     180
gatatggctg gagtggagga cctgatggac actatcgagg aagttaaacc ttgctggacc     240
aaaccaagtc caaaaaatca gccatctaat ggttttgtta cattctcctt gactatgggc     300
cctgaatatc acatctcaca gatcacagat gctgtggttg ttgcgaggta tctaggtgca     360
acatttgtac tcccagacat cagaggaaat gaattaggaa ataagcgaaa attccaagac     420
atgtacaatg tggataaatt cgtgaggagc ctagatggtg ttgtcgaagt aatagatgaa     480
atacctgatg aagtgagtgc taagaagcca gcagttatca gagtaccaaa ccgtgtgact     540
gaaagcttca tcatggacac catccagccc atctttaaaa aaaacaagta cttaagactt     600
gcggtcattt tctcttcagt aagtttaagg ccaaaggaga cgagtaacaa ggacttggat     660
gcgactgctt gccttgcaat gttcagtggc ctcgaactga agcatgaata ttctgaagtc     720
gccagaaaaa tgttggatag gcttcaagaa ttaagcaaga aatcagatgg gaaggtcttg     780
gcaatcgatt gcggaccgga cttgctggaa aagaagagtt gcaagacaac cagtggcgct     840
cgaagaaaag gctgctataa ccctaatgag gtcctggctt tcctgaggag tgttggcttc     900
tctgctaata ctaccatcta cttgacagag acatggtggc acaaaggcct gaatgatctg     960
aaggaggaat tccaaatac ttataccaag gatgacatta tgccagctga aacaaaggt    1020 gaattcctga atccagcaa tgcagaccta gcaagcgctt ggaccttga gatctgctcg    1080 cagagtgacg tgttcatccc tgctgtcgct ggcctgttct acgggcatgt cacaggtaag   1140
aggattgcat ctggtcgtac ccagatcatt gtgccttctc agtccagcac ctcgactcat   1200
gcttcagatt tcacctccac ctacatctcc aacaagaacc acctagccta cacatgctac   1260
tgttag                                                             1266
```

```
<210> SEQ ID NO 52
<211> LENGTH: 421
<212> TYPE: PRT
<213> ORGANISM: Zea mays

<400> SEQUENCE: 52
```

| | | | | | | | | | | | | | | |
|---|---|---|---|---|---|---|---|---|---|---|---|---|---|---|
| Met | Ala | Val | Asp | Pro | Arg | Gln | Val | Val | Ala | Gly | Phe | Leu | Thr | Leu | Ser |
| 1 | | | | 5 | | | | | 10 | | | | | 15 | |
| Met | Phe | Val | Met | Leu | Gly | Asn | Met | Ile | Lys | His | Asp | His | Phe | Ser | Pro |
| | | | 20 | | | | | 25 | | | | | 30 | | |
| Val | Thr | Glu | Glu | Met | Gly | Leu | Lys | Ala | Thr | Gly | Ala | Arg | Ser | Asn | Thr |
| | | 35 | | | | | 40 | | | | | 45 | | | |
| Met | Lys | Leu | Asp | Asn | Asn | Ala | Glu | Met | Asn | Ser | Val | Asp | Met | Ala | Gly |
| | 50 | | | | | 55 | | | | | 60 | | | | |
| Val | Glu | Asp | Leu | Met | Asp | Thr | Ile | Glu | Val | Lys | Pro | Cys | Trp | Thr |
| 65 | | | | 70 | | | | | 75 | | | | | 80 |
| Lys | Pro | Ser | Pro | Lys | Asn | Gln | Pro | Ser | Asn | Gly | Phe | Val | Thr | Phe | Ser |
| | | | | 85 | | | | | 90 | | | | | 95 | |
| Leu | Thr | Met | Gly | Pro | Glu | Tyr | His | Ile | Ser | Gln | Ile | Thr | Asp | Ala | Val |
| | | | 100 | | | | | 105 | | | | | 110 | | |
| Val | Val | Ala | Arg | Tyr | Leu | Gly | Ala | Thr | Phe | Val | Leu | Pro | Asp | Ile | Arg |
| | | | 115 | | | | | 120 | | | | | 125 | | |
| Gly | Asn | Glu | Leu | Gly | Asn | Lys | Arg | Lys | Phe | Gln | Asp | Met | Tyr | Asn | Val |
| | 130 | | | | | 135 | | | | | 140 | | | | |
| Asp | Lys | Phe | Val | Arg | Ser | Leu | Asp | Gly | Val | Val | Glu | Val | Ile | Asp | Glu |
| 145 | | | | | 150 | | | | | 155 | | | | | 160 |
| Ile | Pro | Asp | Glu | Val | Ser | Ala | Lys | Lys | Pro | Ala | Val | Ile | Arg | Val | Pro |
| | | | | 165 | | | | | 170 | | | | | 175 | |
| Asn | Arg | Val | Thr | Glu | Ser | Phe | Ile | Met | Asp | Thr | Ile | Gln | Pro | Ile | Phe |
| | | | 180 | | | | | 185 | | | | | 190 | | |
| Lys | Lys | Asn | Lys | Tyr | Leu | Arg | Leu | Ala | Val | Ile | Phe | Ser | Ser | Val | Ser |
| | | 195 | | | | | 200 | | | | | 205 | | | |
| Leu | Arg | Pro | Lys | Glu | Thr | Ser | Asn | Lys | Asp | Leu | Asp | Ala | Thr | Ala | Cys |
| | 210 | | | | | 215 | | | | | 220 | | | | |
| Leu | Ala | Met | Phe | Ser | Gly | Leu | Glu | Leu | Lys | His | Glu | Tyr | Ser | Glu | Val |
| 225 | | | | | 230 | | | | | 235 | | | | | 240 |
| Ala | Arg | Lys | Met | Leu | Asp | Arg | Leu | Gln | Glu | Leu | Ser | Lys | Lys | Ser | Asp |
| | | | | 245 | | | | | 250 | | | | | 255 | |
| Gly | Lys | Val | Leu | Ala | Ile | Asp | Leu | Arg | Thr | Asp | Leu | Leu | Glu | Lys | Lys |
| | | | 260 | | | | | 265 | | | | | 270 | | |
| Ser | Cys | Lys | Thr | Thr | Ser | Gly | Ala | Arg | Arg | Lys | Gly | Cys | Tyr | Asn | Pro |
| | | 275 | | | | | 280 | | | | | 285 | | | |
| Asn | Glu | Val | Leu | Ala | Phe | Leu | Arg | Ser | Val | Gly | Phe | Ser | Ala | Asn | Thr |
| | 290 | | | | | 295 | | | | | 300 | | | | |
| Thr | Ile | Tyr | Leu | Thr | Glu | Thr | Trp | Trp | His | Lys | Gly | Leu | Asn | Asp | Leu |
| 305 | | | | | 310 | | | | | 315 | | | | | 320 |
| Lys | Glu | Glu | Phe | Pro | Asn | Thr | Tyr | Thr | Lys | Asp | Ile | Met | Pro | Ala |
| | | | | 325 | | | | | 330 | | | | | 335 |
| Glu | Asn | Lys | Gly | Glu | Phe | Leu | Lys | Ser | Ser | Asn | Ala | Asp | Leu | Ala | Ser |
| | | | 340 | | | | | 345 | | | | | 350 | | |
| Ala | Leu | Asp | Leu | Glu | Ile | Cys | Ser | Gln | Ser | Asp | Val | Phe | Ile | Pro | Ala |
| | | 355 | | | | | 360 | | | | | 365 | | | |
| Val | Ala | Gly | Leu | Phe | Tyr | Gly | His | Val | Thr | Gly | Lys | Arg | Ile | Ala | Ser |
| | 370 | | | | | 375 | | | | | 380 | | | | |

```
Gly Arg Thr Gln Ile Ile Val Pro Ser Gln Ser Thr Ser Thr His
385                 390                 395                 400

Ala Ser Asp Phe Thr Ser Thr Tyr Ile Ser Asn Lys Asn His Leu Ala
            405                 410                 415

Tyr Thr Cys Tyr Cys
            420

<210> SEQ ID NO 53
<211> LENGTH: 3024
<212> TYPE: DNA
<213> ORGANISM: Oryza sativa

<400> SEQUENCE: 53
```

| | | | | | |
|---|---|---|---|---|---|
| atgccaccgc | cctcccttct | cctccctcct | ctcctcctcc | tcctcggcct | ccatgccgcc | 60 |
| gccgccgccg | tctccgaggt | gtcggccctc | atggccttca | agaacgccct | caccatccct | 120 |
| cccaccgccg | ccgccttctt | cgcccggtgg | gacgccgccg | cggcttcccc | ctgcaacttc | 180 |
| accgcgtcg | actgcgccaa | ttccggcggc | ggcggcgtca | ccgccgtcgc | cgtggagggc | 240 |
| ttgggcgtgg | ccgcaacgtc | cgtcccgttc | gacgttctgt | gcggctcgct | gccgtcgctc | 300 |
| gcgaagctct | ccctgccgtc | gaacgcgctc | gccgggggga | tcggcggcgt | cgcggggtgc | 360 |
| accgccctcg | aggtgctcga | cctcgcgttc | aatggcttct | ccggccacgt | cccggacctc | 420 |
| tcgccgctga | cgaggctgca | gaggctcaac | gtgtcgcaga | acagcttcac | cggcgccttc | 480 |
| ccatggcgcg | cgctggcgtc | catgccgggt | ctcaccgtgc | tcgccgccgg | cgacaatggg | 540 |
| ttcttcgaga | gacggagac | gttccccgac | gagatcaccg | cgctcaccaa | cctcaccgtg | 600 |
| ctctacctct | ccgcggccaa | catcggcggc | gtcatccctc | ccggcatcgg | caacctcgcc | 660 |
| aagctcgtcg | acctcgagct | ctccgacaac | gcgctcaccg | gcgagatacc | gccggagatc | 720 |
| accaagctca | ccaacctcct | gcagctcgag | ctgtacaaca | actcgctcca | cggcgagctc | 780 |
| ccggcggggt | cgggaaacct | gacgaagctc | cagttcttcg | acgcgtccat | gaaccacctc | 840 |
| accggcagcc | tctccgagct | ccggtcgctc | acccagctcg | tgtcgctgca | gctgttctac | 900 |
| aatggcttca | ccggcgacgt | gccgccggag | ttcggcgagt | tcaaggagct | cgtgaacctg | 960 |
| tccctgtaca | caacaaccct | caccggcgag | ctgccgcggg | atctcggcag | ctgggcggag | 1020 |
| ttcaacttca | tcgacgtgtc | caccaacgcg | ctgtccggcc | cgatcccgcc | gttcatgtgc | 1080 |
| aagcgcggca | agatgaccag | gctgctcatg | ctggagaaca | cttctccgg | ccagattccg | 1140 |
| gccacctacg | caaactgcac | gacgctggtg | aggttcaggg | tgagcaagaa | ctccatgtcc | 1200 |
| ggcgacgtcc | ccgacgggtt | gtgggcgctc | cccaacgtcg | acatcattga | cctcgccaac | 1260 |
| aaccagttca | ccgggggggat | cggcgacggc | atcgggagag | ccgccttgct | gagcagcctc | 1320 |
| gacctggccg | gaacaggtt | ctccggcgcg | atcccgccgt | cgatcggcga | cgccagcaac | 1380 |
| ctcgagacaa | ttgacatttc | gtcgaacggg | ttgtcgggca | aaattccggc | gagcatcggg | 1440 |
| aggctggcac | gtctcggcag | cttgaacatt | gctaggaatg | gatcaccgg | ggccatcccg | 1500 |
| gcgagcatcg | gcgagtgctc | gtcgcttagt | acggtcaatt | tcaccgggaa | caagctcgcc | 1560 |
| ggcgcgatcc | cgtcggagct | ggggaccctg | ccgcggctta | attctttgga | cttgtccggg | 1620 |
| aatgacctct | ccggtgccgt | gccggcgagc | ctcgccgctc | tgaagctgag | ctccctgaac | 1680 |
| atgtccgaca | caagctcgt | cgggcccgtg | ccggagccgc | tctccatcgc | ggcctacggc | 1740 |
| gagagcttca | gggggaaccc | cgggctgtgc | gccaccaacg | gagtggactt | cctccgccgc | 1800 |
| tgctcgccgg | gatcaggagg | ccactccgcg | gccaccgcgc | gcaccgtggt | cacctgcctc | 1860 |

```
ctcgccggcc tcgccgtagt gctcgcggcg ctcggcgcgg tgatgtacat caagaagcgg    1920
cggcgcgcgg aggcggaggc ggaggaggcg gccggcggca aggtgttcgg caagaagggg    1980
tcgtgggacc tcaagtcgtt cagggtcctg gcgttcgacg agcacgaggt gatcgacggt    2040
gtccgcgacg agaacctcat cggcagcggc gggtccggga acgtgtaccg cgtgaagctc    2100
gggagcggcg cggtggtcgc ggtgaagcac atcacccgga cacgcgcggc ggcggcggcg    2160
gcgaggagca cggcggcgtc ggccgccatg ctccgttcgc cgtcggcggc gcggcgcacg    2220
gcgtcggtgc ggtgccgcga gttcgactcg gaggtgggga cgctgagctc gatccggcac    2280
gtgaacgtgg tgaagctcct gtgcagcatc accagcgacg acggcgcggc gagcctgctg    2340
gtgtacgagc acctccccaa tggcagcctc tacgagcgcc tgcacgaggg gcaaaagctc    2400
ggcggccgcg gcggcctcgg gtggccggag cgctacgaca tcgccgtcgg cgccgcccgt    2460
gggctggagt acctccacca cggctgcgac cgccccatcc tccaccgtga cgtcaagtcc    2520
agcaacatcc tcctcgacga gtccttcaag ccgcgcatcg ccgacttcgg cctcgccaag    2580
atcctcgacg gcgccgccgc cacgccggac accaccagcg cgggcgtggt ggccggcacg    2640
ctcgggtaca tggcgcccga gtactcctac acgtggaagg tgacggagaa gagcgacgtg    2700
tacagcttcg gcgtggtgct gcttgagctg gtgacggggc ggacggcgat catggcggag    2760
tacggggaga gtaggggaca tcgtggagtgg gtgtctcgcc ggttagatag ccgagacaag    2820
gtgatgtccc cctcgacgc cagcatcggc gaggaatggg agaaggagga ggccgtcagg    2880
gtgcttcgcg tcgccgtggt gtgcaccagc aggacgccgt cgatgaggcc gtcgatgcgc    2940
tccgtcgtgc agatgctcga ggcggcggcg atcggccggg agttcgccgt ggtcacttcg    3000
gtgaaggtca aggtgatccc ctag                                           3024
```

<210> SEQ ID NO 54
<211> LENGTH: 1007
<212> TYPE: PRT
<213> ORGANISM: Oryza sativa

<400> SEQUENCE: 54

```
Met Pro Pro Pro Ser Leu Leu Pro Leu Leu Leu Leu Gly
 1               5                  10              15

Leu His Ala Ala Ala Ala Val Ser Glu Val Ser Ala Leu Met Ala
                20                  25                  30

Phe Lys Asn Ala Leu Thr Ile Pro Thr Ala Ala Ala Phe Phe Ala
            35                  40                  45

Arg Trp Asp Ala Ala Ala Ser Pro Cys Asn Phe Thr Gly Val Asp
    50                  55                  60

Cys Ala Asn Ser Gly Gly Gly Val Thr Ala Val Ala Val Glu Gly
65                  70                  75                  80

Leu Gly Val Ala Ala Thr Ser Val Pro Phe Asp Val Leu Cys Gly Ser
                85                  90                  95

Leu Pro Ser Leu Ala Lys Leu Ser Leu Pro Ser Asn Ala Leu Ala Gly
            100                 105                 110

Gly Ile Gly Gly Val Ala Gly Cys Thr Ala Leu Glu Val Leu Asp Leu
        115                 120                 125

Ala Phe Asn Gly Phe Ser Gly His Val Pro Asp Leu Ser Pro Leu Thr
    130                 135                 140

Arg Leu Gln Arg Leu Asn Val Ser Gln Asn Ser Phe Thr Gly Ala Phe
145                 150                 155                 160

Pro Trp Arg Ala Leu Ala Ser Met Pro Gly Leu Thr Val Leu Ala Ala
```

```
              165                 170                 175
Gly Asp Asn Gly Phe Glu Lys Thr Glu Thr Phe Pro Asp Glu Ile
            180                 185                 190
Thr Ala Leu Thr Asn Leu Thr Val Leu Tyr Leu Ser Ala Ala Asn Ile
            195                 200                 205
Gly Gly Val Ile Pro Pro Gly Ile Gly Asn Leu Ala Lys Leu Val Asp
            210                 215                 220
Leu Glu Leu Ser Asp Asn Ala Leu Thr Gly Ile Pro Pro Glu Ile
225                 230                 235                 240
Thr Lys Leu Thr Asn Leu Leu Gln Leu Glu Leu Tyr Asn Asn Ser Leu
                245                 250                 255
His Gly Glu Leu Pro Ala Gly Phe Gly Asn Leu Thr Lys Leu Gln Phe
                260                 265                 270
Phe Asp Ala Ser Met Asn His Leu Thr Gly Ser Leu Ser Glu Leu Arg
                275                 280                 285
Ser Leu Thr Gln Leu Val Ser Leu Gln Leu Phe Tyr Asn Gly Phe Thr
            290                 295                 300
Gly Asp Val Pro Pro Glu Phe Gly Glu Phe Lys Glu Leu Val Asn Leu
305                 310                 315                 320
Ser Leu Tyr Asn Asn Asn Leu Thr Gly Glu Leu Pro Arg Asp Leu Gly
                325                 330                 335
Ser Trp Ala Glu Phe Asn Phe Ile Asp Val Ser Thr Asn Ala Leu Ser
                340                 345                 350
Gly Pro Ile Pro Pro Phe Met Cys Lys Arg Gly Lys Met Thr Arg Leu
                355                 360                 365
Leu Met Leu Glu Asn Asn Phe Ser Gly Gln Ile Pro Ala Thr Tyr Ala
            370                 375                 380
Asn Cys Thr Thr Leu Val Arg Phe Arg Val Ser Lys Asn Ser Met Ser
385                 390                 395                 400
Gly Asp Val Pro Asp Gly Leu Trp Ala Leu Pro Asn Val Asp Ile Ile
                405                 410                 415
Asp Leu Ala Asn Asn Gln Phe Thr Gly Gly Ile Gly Asp Gly Ile Gly
                420                 425                 430
Arg Ala Ala Leu Leu Ser Ser Leu Asp Leu Ala Gly Asn Arg Phe Ser
            435                 440                 445
Gly Ala Ile Pro Pro Ser Ile Gly Asp Ala Ser Asn Leu Glu Thr Ile
            450                 455                 460
Asp Ile Ser Ser Asn Gly Leu Ser Gly Lys Ile Pro Ala Ser Ile Gly
465                 470                 475                 480
Arg Leu Ala Arg Leu Gly Ser Leu Asn Ile Ala Arg Asn Gly Ile Thr
                485                 490                 495
Gly Ala Ile Pro Ala Ser Ile Gly Glu Cys Ser Ser Leu Ser Thr Val
            500                 505                 510
Asn Phe Thr Gly Asn Lys Leu Ala Gly Ala Ile Pro Ser Glu Leu Gly
            515                 520                 525
Thr Leu Pro Arg Leu Asn Ser Leu Asp Leu Ser Gly Asn Asp Leu Ser
            530                 535                 540
Gly Ala Val Pro Ala Ser Leu Ala Leu Lys Leu Ser Ser Leu Asn
545                 550                 555                 560
Met Ser Asp Asn Lys Leu Val Gly Pro Val Pro Glu Pro Leu Ser Ile
                565                 570                 575
Ala Ala Tyr Gly Glu Ser Phe Lys Gly Asn Pro Gly Leu Cys Ala Thr
            580                 585                 590
```

-continued

Asn Gly Val Asp Phe Leu Arg Arg Cys Ser Pro Gly Ser Gly Gly His
        595                 600                 605

Ser Ala Ala Thr Ala Arg Thr Val Val Thr Cys Leu Leu Ala Gly Leu
    610                 615                 620

Ala Val Val Leu Ala Ala Leu Gly Ala Val Met Tyr Ile Lys Lys Arg
625                 630                 635                 640

Arg Arg Ala Glu Ala Glu Ala Glu Glu Ala Gly Gly Lys Val Phe
            645                 650                 655

Gly Lys Lys Gly Ser Trp Asp Leu Lys Ser Phe Arg Val Leu Ala Phe
                660                 665                 670

Asp Glu His Glu Val Ile Asp Gly Val Arg Asp Glu Asn Leu Ile Gly
            675                 680                 685

Ser Gly Gly Ser Gly Asn Val Tyr Arg Val Lys Leu Gly Ser Gly Ala
        690                 695                 700

Val Val Ala Val Lys His Ile Thr Arg Thr Arg Ala Ala Ala Ala Ala
705                 710                 715                 720

Ala Arg Ser Thr Ala Ala Ser Ala Ala Met Leu Arg Ser Pro Ser Ala
            725                 730                 735

Ala Arg Arg Thr Ala Ser Val Arg Cys Arg Glu Phe Asp Ser Glu Val
            740                 745                 750

Gly Thr Leu Ser Ser Ile Arg His Val Asn Val Val Lys Leu Leu Cys
        755                 760                 765

Ser Ile Thr Ser Asp Asp Gly Ala Ala Ser Leu Leu Val Tyr Glu His
        770                 775                 780

Leu Pro Asn Gly Ser Leu Tyr Glu Arg Leu His Glu Gly Gln Lys Leu
785                 790                 795                 800

Gly Gly Arg Gly Gly Leu Gly Trp Pro Glu Arg Tyr Asp Ile Ala Val
                805                 810                 815

Gly Ala Ala Arg Gly Leu Glu Tyr Leu His His Gly Cys Asp Arg Pro
            820                 825                 830

Ile Leu His Arg Asp Val Lys Ser Ser Asn Ile Leu Leu Asp Glu Ser
        835                 840                 845

Phe Lys Pro Arg Ile Ala Asp Phe Gly Leu Ala Lys Ile Leu Asp Gly
    850                 855                 860

Ala Ala Ala Thr Pro Asp Thr Thr Ser Ala Gly Val Val Ala Gly Thr
865                 870                 875                 880

Leu Gly Tyr Met Ala Pro Glu Tyr Ser Tyr Thr Trp Lys Val Thr Glu
            885                 890                 895

Lys Ser Asp Val Tyr Ser Phe Gly Val Val Leu Leu Glu Leu Val Thr
            900                 905                 910

Gly Arg Thr Ala Ile Met Ala Glu Tyr Gly Glu Ser Arg Asp Ile Val
        915                 920                 925

Glu Trp Val Ser Arg Arg Leu Asp Ser Arg Asp Lys Val Met Ser Leu
    930                 935                 940

Leu Asp Ala Ser Ile Glu Glu Trp Glu Lys Glu Glu Ala Val Arg
945                 950                 955                 960

Val Leu Arg Val Ala Val Val Cys Thr Ser Arg Thr Pro Ser Met Arg
            965                 970                 975

Pro Ser Met Arg Ser Val Val Gln Met Leu Glu Ala Ala Ala Ile Gly
            980                 985                 990

Arg Glu Phe Ala Val Val Thr Ser   Val Lys Val Lys Val  Ile Pro
        995                 1000                1005

<210> SEQ ID NO 55
<211> LENGTH: 2970
<212> TYPE: DNA
<213> ORGANISM: Zea mays

<400> SEQUENCE: 55

| | |
|---|---|
| atgccgcccg cctccccct cctcttcgtc ttcctcgccg ccgccatcgt cgcctgcgcc | 60 |
| accgcagcga cgtcgacgtc gacgtcgtcc caggcggacg cgctccaggc cttcagggcc | 120 |
| gccctcaccg tcccgcccga ggccgctccc ttcttcgcca cgtggagcgc caccgcggca | 180 |
| tccccctgcg gcttcacggg cgtcaactgc accggcggca acgtcacggc gctctccctg | 240 |
| ccggcactca agctgtccgc cgcgacggtc ccgttcgccg ccctctgcgc cgccctgcct | 300 |
| tccctcgccg cgctgtccct gccggagaac tccctgcgg cgccatcga cggcgtcgtc | 360 |
| aagtgcaccg cgctccagga gctcaacctc gcgttcaacg gcttcacggg cgccgtgccg | 420 |
| gacctctcgc cgctggccgg gctgcgcagt ctcaacgtct cgtccaactg cttcgacggc | 480 |
| gcgttcccgt ggcgctcgct cgcatacacg ccgggcctca ccctgctcgc gctcggcgac | 540 |
| aacccgttcc tcgcgcccac cgccgcgttc ccgcccgagg tcacgaagct caccaacctc | 600 |
| accgtgctct acatgtccgc cgccaagatc ggaggcgcca tcccgccgga gatcggcgac | 660 |
| ctggtcaacc tcgtcgacct tgagctctcc gacaacgacc tcaccggcga gatcccgccg | 720 |
| gagatcgcca ggctccaccag cctcacccag ctcgagctct acaacaactc cctccggggc | 780 |
| gcgctccccg ccggattcgg caggctcacc aagctgcagt acttggacgc gtcccagaac | 840 |
| cacctcaccg gcagcctcgc cgagctccgc tccctcacgc gctcgtgtc gctgcagctc | 900 |
| ttcttcaacg gcttcaccgg cgaggtgccc ccggagttcg gcgacttccg ggacctcgtc | 960 |
| aacctgtccc tctacagcaa caacctcacc ggcgagctgc cgcggagcct cggcagctgg | 1020 |
| gcgcggttca acttcatcga cgtgtccacc aacttgctct cggggcccat cccgccggac | 1080 |
| atgtgcaagc agggcaccat gctgaagctg ctcatgctcg agaacaactt ctccggcggg | 1140 |
| atcccggaga cgtacgccag ctgcaagacg ctggtgaggt tccgtgtcag caacaacagc | 1200 |
| ctctccggcg aggtgcccga ggggctgtgg gctctcccca cgtcaacgt gctcgaccttt | 1260 |
| gccgggaacc agttcagcgg cagcatcggc gacggaattg ggaacgccgc cgcgatgacc | 1320 |
| aacctcctcc ttgctgggaa ccagttcagc ggcgcggtac cgccgtcgat cggcgacgcg | 1380 |
| gcgagcctcg agagcgtgga cctgtcgcgg aaccagctct ccggcgagat accggagagc | 1440 |
| atcgggagtc tgtcccgtct cggcagcctc aacattgagg ggaacgcgat cggcgggcca | 1500 |
| atcccggcga gcctgggctc ctgctcggcg ttgagcacgg tcaatttcgc tgggaacagg | 1560 |
| ctcgacggcg cgatcccgc ggagctgggc aacctgcagc ggctcaactc cctcgacgtt | 1620 |
| tccccggaacg acctctccgg cgccgtgccg gcgagcctcg cggcgctgaa gctgagcagc | 1680 |
| ctgaacatgt ccgacaacca cctcaccggg cccgttccgg aggcgcttgc gatctcggcc | 1740 |
| tacgcgagag gcttcgacgg gaaccccggg ctgtgtgcca ccaacggcgc tgtcttcctc | 1800 |
| cgccgctgcg gtcggagctc cgggagccgg tcggcgaacg cggagcgcct ggccgtgacg | 1860 |
| tgcatcctcg ccgtcacggc ggtgctgctg cgggggcg cgtggccat gtgcctgcag | 1920 |
| aagcggcggc ggcggcgcgc ggaggcctcc gcggggaagc tgttcgccaa gaagggctcg | 1980 |
| tgggacctca gtcgttccg gatcctggcg ttcgacgagc gggagatcat cgagggcgtc | 2040 |
| cgcgacgaga acctggtcgg cagcggcggg tctgggaacg tgtaccgcgt gaagctcggc | 2100 |
| aacggcgcgg tggtggccgt gaagcacgtc acgcgggggg tggcgacgag cacggcgccg | 2160 |

```
tccgccgcca tgctgcggcc ggcggcgtcg gtgcggtgcc gcgagttcga ctcggaggtg    2220
gggacgctga gcgccatccg gcacgtgaac gtggtgaagc tgctgtgcag catcaccagc    2280
gcggacggcg cggcgagcct gctggtgtac gagcacctcc ccaacggcag cctgtacgag    2340
cggctgcacg gggcggcggg gcggaagctg gcgcgctcg gtgggtgga gcggcacgac    2400 gtggcggtgg gcgcggcgag gggcctcgag tacctccacc acggctgcga ccgccccatc    2460
ctccaccgcg acgtcaagtc cagcaacatc tcctggacg agtcgttcaa gcccggctc    2520 gccgacttcg ggctcgccaa gatcctcagc tcggcaggcg gcggcggcgg ccactcgtcc    2580
gccggcgtcg tggccggcac gctggggtac atggcgccgg agtacgcgta cacgtgcaag    2640
gtgacggaga agagcgacgt gtacagcttc ggcgtggtgc tgctggagct ggtgacgggg    2700
cggccggcgg tggtggagag ccgggacctg gtggactggg tgtcgcggcg gctggagagc    2760
cgggagaagg tgatgtccct ggtggacccg ggcatcgtgg aagggtgggc caggaggag    2820 gcagtccgcg tgctgcgcgt cgccgtgctg tgcaccagcc gcacgccgtc gatgcggccg    2880
tccatgcgct ccgtcgtgca gatgctggag gacgcggccg ccgcgcgcca ggacgacgac    2940
gggaaggtcc tggaggtgaa ggtggtctga                                     2970
```

<210> SEQ ID NO 56
<211> LENGTH: 989
<212> TYPE: PRT
<213> ORGANISM: Zea mays

<400> SEQUENCE: 56

```
Met Pro Pro Ala Ser Pro Leu Leu Phe Val Phe Leu Ala Ala Ala Ile
1               5                   10                  15

Val Ala Cys Ala Thr Ala Ala Thr Ser Thr Ser Thr Ser Ser Gln Ala
            20                  25                  30

Asp Ala Leu Gln Ala Phe Arg Ala Ala Leu Thr Val Pro Pro Glu Ala
        35                  40                  45

Ala Pro Phe Phe Ala Thr Trp Ser Ala Thr Ala Ser Pro Cys Gly
    50                  55                  60

Phe Thr Gly Val Asn Cys Thr Gly Gly Asn Val Thr Ala Leu Ser Leu
65                  70                  75                  80

Pro Ala Leu Lys Leu Ser Ala Ala Thr Val Pro Phe Ala Ala Leu Cys
                85                  90                  95

Ala Ala Leu Pro Ser Leu Ala Ala Leu Ser Leu Pro Glu Asn Ser Leu
            100                 105                 110

Ala Gly Ala Ile Asp Gly Val Val Lys Cys Thr Ala Leu Gln Glu Leu
        115                 120                 125

Asn Leu Ala Phe Asn Gly Phe Thr Gly Ala Val Pro Asp Leu Ser Pro
    130                 135                 140

Leu Ala Gly Leu Arg Ser Leu Asn Val Ser Ser Asn Cys Phe Asp Gly
145                 150                 155                 160

Ala Phe Pro Trp Arg Ser Leu Ala Tyr Thr Pro Gly Leu Thr Leu Leu
                165                 170                 175

Ala Leu Gly Asp Asn Pro Phe Leu Ala Pro Thr Ala Ala Phe Pro Pro
            180                 185                 190

Glu Val Thr Lys Leu Thr Asn Leu Thr Val Leu Tyr Met Ser Ala Ala
        195                 200                 205

Lys Ile Gly Gly Ala Ile Pro Pro Glu Ile Gly Asp Leu Val Asn Leu
    210                 215                 220
```

```
Val Asp Leu Glu Leu Ser Asp Asn Asp Leu Thr Gly Glu Ile Pro Pro
225                 230                 235                 240

Glu Ile Ala Arg Leu Thr Ser Leu Thr Gln Leu Glu Leu Tyr Asn Asn
            245                 250                 255

Ser Leu Arg Gly Ala Leu Pro Ala Gly Phe Gly Arg Leu Thr Lys Leu
            260                 265                 270

Gln Tyr Leu Asp Ala Ser Gln Asn His Leu Thr Gly Ser Leu Ala Glu
        275                 280                 285

Leu Arg Ser Leu Thr Arg Leu Val Ser Leu Gln Leu Phe Phe Asn Gly
    290                 295                 300

Phe Thr Gly Glu Val Pro Pro Glu Phe Gly Asp Phe Arg Asp Leu Val
305                 310                 315                 320

Asn Leu Ser Leu Tyr Ser Asn Asn Leu Thr Gly Glu Leu Pro Arg Ser
                325                 330                 335

Leu Gly Ser Trp Ala Arg Phe Asn Phe Ile Asp Val Ser Thr Asn Leu
            340                 345                 350

Leu Ser Gly Pro Ile Pro Pro Asp Met Cys Lys Gln Gly Thr Met Leu
        355                 360                 365

Lys Leu Leu Met Leu Glu Asn Asn Phe Ser Gly Gly Ile Pro Glu Thr
    370                 375                 380

Tyr Ala Ser Cys Lys Thr Leu Val Arg Phe Arg Val Ser Asn Asn Ser
385                 390                 395                 400

Leu Ser Gly Glu Val Pro Glu Gly Leu Trp Ala Leu Pro Asn Val Asn
                405                 410                 415

Val Leu Asp Leu Ala Gly Asn Gln Phe Ser Gly Ser Ile Gly Asp Gly
            420                 425                 430

Ile Gly Asn Ala Ala Met Thr Asn Leu Leu Leu Ala Gly Asn Gln
        435                 440                 445

Phe Ser Gly Ala Val Pro Pro Ser Ile Gly Asp Ala Ala Ser Leu Glu
    450                 455                 460

Ser Val Asp Leu Ser Arg Asn Gln Leu Ser Gly Glu Ile Pro Glu Ser
465                 470                 475                 480

Ile Gly Ser Leu Ser Arg Leu Gly Ser Leu Asn Ile Glu Gly Asn Ala
                485                 490                 495

Ile Gly Gly Pro Ile Pro Ala Ser Leu Gly Ser Cys Ser Ala Leu Ser
            500                 505                 510

Thr Val Asn Phe Ala Gly Asn Arg Leu Asp Gly Ala Ile Pro Ala Glu
        515                 520                 525

Leu Gly Asn Leu Gln Arg Leu Asn Ser Leu Asp Val Ser Arg Asn Asp
    530                 535                 540

Leu Ser Gly Ala Val Pro Ala Ser Leu Ala Ala Leu Lys Leu Ser Ser
545                 550                 555                 560

Leu Asn Met Ser Asp Asn His Leu Thr Gly Pro Val Pro Glu Ala Leu
                565                 570                 575

Ala Ile Ser Ala Tyr Gly Glu Ser Phe Asp Gly Asn Pro Gly Leu Cys
            580                 585                 590

Ala Thr Asn Gly Ala Val Phe Leu Arg Arg Cys Gly Arg Ser Ser Gly
        595                 600                 605

Ser Arg Ser Ala Asn Ala Glu Arg Leu Ala Val Thr Cys Ile Leu Ala
    610                 615                 620

Val Thr Ala Val Leu Leu Ala Gly Ala Gly Val Ala Met Cys Leu Gln
625                 630                 635                 640

Lys Arg Arg Arg Arg Arg Ala Glu Ala Ser Ala Gly Lys Leu Phe Ala
```

```
                    645                 650                 655
Lys Lys Gly Ser Trp Asp Leu Lys Ser Phe Arg Ile Leu Ala Phe Asp
            660                 665                 670

Glu Arg Glu Ile Ile Glu Gly Val Arg Asp Glu Asn Leu Val Gly Ser
        675                 680                 685

Gly Gly Ser Gly Asn Val Tyr Arg Val Lys Leu Gly Asn Gly Ala Val
    690                 695                 700

Val Ala Val Lys His Val Thr Arg Gly Val Ala Thr Ser Thr Ala Pro
705                 710                 715                 720

Ser Ala Ala Met Leu Arg Pro Ala Ala Ser Val Arg Cys Arg Glu Phe
            725                 730                 735

Asp Ser Glu Val Gly Thr Leu Ser Ala Ile Arg His Val Asn Val Val
        740                 745                 750

Lys Leu Leu Cys Ser Ile Thr Ser Ala Asp Gly Ala Ala Ser Leu Leu
    755                 760                 765

Val Tyr Glu His Leu Pro Asn Gly Ser Leu Tyr Glu Arg Leu His Gly
770                 775                 780

Ala Ala Gly Arg Lys Leu Gly Ala Leu Gly Trp Val Glu Arg His Asp
785                 790                 795                 800

Val Ala Val Gly Ala Ala Arg Gly Leu Glu Tyr Leu His His Gly Cys
            805                 810                 815

Asp Arg Pro Ile Leu His Arg Asp Val Lys Ser Ser Asn Ile Leu Leu
        820                 825                 830

Asp Glu Ser Phe Lys Pro Arg Leu Ala Asp Phe Gly Leu Ala Lys Ile
    835                 840                 845

Leu Ser Ser Ala Gly Gly Gly Gly His Ser Ser Ala Gly Val Val
850                 855                 860

Ala Gly Thr Leu Gly Tyr Met Ala Pro Glu Tyr Ala Tyr Thr Cys Lys
865                 870                 875                 880

Val Thr Glu Lys Ser Asp Val Tyr Ser Phe Gly Val Val Leu Leu Glu
            885                 890                 895

Leu Val Thr Gly Arg Pro Ala Val Val Glu Ser Arg Asp Leu Val Asp
        900                 905                 910

Trp Val Ser Arg Arg Leu Glu Ser Arg Glu Lys Val Met Ser Leu Val
    915                 920                 925

Asp Pro Gly Ile Val Glu Gly Trp Ala Arg Glu Ala Val Arg Val
930                 935                 940

Leu Arg Val Ala Val Leu Cys Thr Ser Arg Thr Pro Ser Met Arg Pro
945                 950                 955                 960

Ser Met Arg Ser Val Val Gln Met Leu Glu Asp Ala Ala Ala Arg
            965                 970                 975

Gln Asp Asp Asp Gly Lys Val Leu Glu Val Lys Val Val
        980                 985

<210> SEQ ID NO 57
<211> LENGTH: 1389
<212> TYPE: DNA
<213> ORGANISM: Oryza sativa

<400> SEQUENCE: 57
atgcccaata acgctcagtg ccaagtcgtc gatgacaggc tcagcgcgct cccggatgaa      60
attttgattg acatcctcca acggctgcaa ctgccgactg cagcccggac caccactctt     120
gcaagaagat ggacccatct tctccaatcc atgaaccatc ttgaaatcga tgttgccgat     180
```

```
ttcataccac gccggtctgc tccttcactc aaaaggaaca ccatgactcg agtcaaggtg    240
gccatgtcaa ggacactgca cctgtgcttc tacctcactg acccttacct gcactccgtt    300
gggcgcatgc ttgaggatgc agttcagagt gccggtggca gagcaagcaa gattgaggtc    360
ctttcctttt ccatcctgac cgaggtgcct gagctgcttt gtaccgagaa cacctggca     420
cgatatggga gacgcttcat gtccttcttt caagcttacc ccaatgcatt caggcgactg    480
acaagcctct ctctgtgggc tctcaggttt ggggattcag acatccccaa cctcctagcc    540
tcctgcctcc agctgcagca cctcaccctg caggattgcg ataatggcaa gaggtatgtg    600
ctcagaatcg atgcaccaaa ctcgcagctc agcacgctga cgatggcctt ctgcagttac    660
atcaaggttg agctcatcaa cgctcccaag ctgaaatgcg tggactgtga tacatgggtg    720
ggtgccaatc ctcctgtttg tttcggctgc gtcccaatgc ttgaccggat acgtttctct    780
tccacctgcc acaagatgca gctgccattc aagctcagcg actggctgtc gaccgtgcca    840
actctaacta gtttgcatct ggacttccag gatgagatgg tttggatcct gccagaagag    900
cccaagaaac tcttccccat attccgcaat cttaggaatg tatatctttg cagcattagt    960
cttgattgtg gcctcgactg gactctcttt gtccttgaag gcgcacccct cctcgagcga   1020
tttcatgtta agatatctct ccacatatgt gacgagaatg gctttaagga cagggctgac   1080
agaagcaatg ttgtgtggga agcatcatct gaaagcatca agcataagac cttgaggttg   1140
ctggatataa acggctttga gaccactgag aatctgatca agtacataag gcttgtcatt   1200
cagagagctg tggggctaca gcgaattcac ttgcatgata aggaaccgtg cgaagattgc   1260
gatggtattt atctcaatac gccatctctg tccagaacta tattccccaa caatgaggca   1320
gagaaggatc tgttaagaca gcaactcctg cagggattct cctcatctat agagataaca   1380
ataggttag                                                            1389
```

<210> SEQ ID NO 58
<211> LENGTH: 462
<212> TYPE: PRT
<213> ORGANISM: Oryza sativa

<400> SEQUENCE: 58

```
Met Pro Asn Asn Ala Gln Cys Gln Val Val Asp Asp Arg Leu Ser Ala
1               5                   10                  15

Leu Pro Asp Glu Ile Leu Ile Asp Ile Leu Gln Arg Leu Gln Leu Pro
            20                  25                  30

Thr Ala Ala Arg Thr Thr Thr Leu Ala Arg Arg Trp Thr His Leu Leu
        35                  40                  45

Gln Ser Met Asn His Leu Glu Ile Asp Val Ala Asp Phe Ile Pro Arg
    50                  55                  60

Arg Ser Ala Pro Ser Leu Lys Arg Asn Thr Met Thr Arg Val Lys Val
65                  70                  75                  80

Ala Met Ser Arg Thr Leu His Leu Cys Phe Tyr Leu Thr Asp Pro Tyr
                85                  90                  95

Leu His Ser Val Gly Arg Met Leu Glu Asp Ala Val Gln Ser Ala Gly
            100                 105                 110

Gly Arg Ala Ser Lys Ile Glu Val Leu Ser Phe Ser Ile Leu Thr Glu
        115                 120                 125

Val Pro Glu Leu Leu Cys Thr Glu Lys His Leu Ala Arg Tyr Gly Arg
    130                 135                 140

Arg Phe Met Ser Phe Phe Gln Ala Tyr Pro Asn Ala Phe Arg Arg Leu
145                 150                 155                 160
```

Thr Ser Leu Ser Leu Trp Ala Leu Arg Phe Gly Asp Ser Asp Ile Pro
         165                 170                 175

Asn Leu Leu Ala Ser Cys Leu Gln Leu Gln His Leu Thr Leu Gln Asp
             180                 185                 190

Cys Asp Asn Gly Lys Arg Tyr Val Leu Arg Ile Asp Ala Pro Asn Ser
         195                 200                 205

Gln Leu Ser Thr Leu Thr Met Ala Phe Cys Ser Tyr Ile Lys Val Glu
         210                 215                 220

Leu Ile Asn Ala Pro Lys Leu Lys Cys Val Asp Cys Asp Thr Trp Val
225                 230                 235                 240

Gly Ala Asn Pro Pro Val Cys Phe Gly Cys Val Pro Met Leu Asp Arg
                 245                 250                 255

Ile Arg Phe Ser Ser Thr Cys His Lys Met Gln Leu Pro Phe Lys Leu
             260                 265                 270

Ser Asp Trp Leu Ser Thr Val Pro Thr Leu Thr Ser Leu His Leu Asp
         275                 280                 285

Phe Gln Asp Glu Met Val Trp Ile Leu Pro Glu Glu Pro Lys Lys Leu
         290                 295                 300

Phe Pro Ile Phe Arg Asn Leu Arg Asn Val Tyr Leu Cys Ser Ile Ser
305                 310                 315                 320

Leu Asp Cys Gly Leu Asp Trp Thr Leu Phe Val Leu Glu Gly Ala Pro
                 325                 330                 335

Phe Leu Glu Arg Phe His Val Lys Ile Ser Leu His Ile Cys Asp Glu
             340                 345                 350

Asn Gly Phe Lys Asp Arg Ala Asp Arg Ser Asn Val Val Trp Glu Ala
         355                 360                 365

Ser Ser Glu Ser Ile Lys His Lys Thr Leu Arg Leu Leu Asp Ile Asn
         370                 375                 380

Gly Phe Glu Thr Thr Glu Asn Leu Ile Lys Tyr Ile Arg Leu Val Ile
385                 390                 395                 400

Gln Arg Ala Val Gly Leu Gln Arg Ile His Leu His Asp Lys Glu Pro
                 405                 410                 415

Cys Glu Asp Cys Asp Gly Ile Tyr Leu Asn Thr Pro Ser Leu Ser Arg
             420                 425                 430

Thr Ile Phe Pro Asn Asn Glu Ala Glu Lys Asp Leu Leu Arg Gln Gln
         435                 440                 445

Leu Leu Gln Gly Phe Ser Ser Ser Ile Glu Ile Thr Ile Gly
         450                 455                 460

<210> SEQ ID NO 59
<211> LENGTH: 1701
<212> TYPE: DNA
<213> ORGANISM: Oryza sativa

<400> SEQUENCE: 59
atggaggcag ggcagcagag tgaggagacg ccactgattc agcagctgcc tccggaggaa      60
caatgttcac aatacacatg tgatggaaca gttaatagtg acaaaaagcc tgcactgaag     120
cagagtacag gcattggag agcatgcttc ttcattttag gtgctcaatt cgctgaaacc      180
ttgtgcttct tcatggtttc gaagaactta gtcatgtacc tcacgagtgc gctgcacgaa     240
agcaacatcg acgctgcaca agtgtgtct atttggatcg gcacttcctt cttcacacca     300
ctcattggag ccttccttgg ctgatacatat tggggaagat actggacgac agttatttcc    360
ctctttatta tcatcatcgg aatgctcatt gtgacggttt catcatcacc attgttcctg    420

```
aattcttctt actacaattg aacatttgc cgtgccacgg tctacacagg gctctacctt      480
actgccgttg aagtggatg tatgaagccc tgcattccag cctttggagc cgatcaattt      540
gacagtgctg acccggtgga acggctggcg aagggctcat tcttcaactg gtattacttc    600
tcaatgaacg tcggctcact gctgtcgacg actctgcttg tctgggtggt ggccaacata    660
gggtggagcg tcggttttgc gatcccgatg ctactctcgg ggttcggcct cgccctgttt    720
ttcgctggta ggaaggttta caggtacaag aaacagggag ggagtccact gacaagggtg    780
tcccaggtgg tggttgcagc tgtaaggaat cataggctga aattgcctga cgatagctca    840
ctcctgcatg aggtttcaaa agtgactgaa gatgattaca ggactcaact caccactcaa    900
ttcaggttct ttgacaaggc tgccatcttg tccgacgaga tctcgccggc gcagtggagc    960
ccgtggaggc tgtgcacggt ttcgcaggtg gaggagctga agatcctgct gcggatgttc    1020
ccggtctggg tgtccatggt cgtcttcttc gtggtgaccg cgcagattac gtcgacgctg    1080
atcgagcagg gcatggccat ggacggccgc gtcggcccgt tcacccttcc ggccgcctca    1140
atcgccacct tcgacgtcat cagcgtcctc gtctgggtcc ccgtctacga caccgtgctg    1200
gtgccactgg cacggcgcgt caccggcaag gaccgtggca tctcccacct gcagcgcatt    1260
ggcgtcggcc tcgcgctcgc cgcggtggcc atggcgtact cggcggtggt cgaggcacgg    1320
cggctgggga cggcgccagc gccggtgagc atcatgtggc aggcgccgtc gtacctggtg    1380
ctgggcgtgg cggaggcgtt cagcgtgatc ggcatgatgg agttcttcta cgagcagtcg    1440
ccggagtcga tgaagagcct gtgcacggcg ctcgggcagc tcgccatcgc ggtcgccaac    1500
tacctcaact ccggcgtgct cgtcgtggtg gcggcggcca ccacgcgcgg cggcggggcc    1560
ggctggatcc cggacaacct cgacgagggg cacctggact acttcttctg gatgatggct    1620
gttgttagcg tcctcaacct gctgcacttc ttgcattgct caatcagata tagagccaat    1680
aacaacacgc tgtcgtcttg a                                                1701
```

<210> SEQ ID NO 60
<211> LENGTH: 566
<212> TYPE: PRT
<213> ORGANISM: Oryza sativa

<400> SEQUENCE: 60

```
Met Glu Ala Gly Ala Ala Asp Glu Glu Thr Pro Leu Ile Gln Gln Leu
1               5                   10                  15

Pro Pro Glu Glu Gln Cys Ser Gln Tyr Thr Cys Asp Gly Thr Val Asn
            20                  25                  30

Ser Asp Lys Lys Pro Ala Leu Lys Gln Ser Thr Gly His Trp Arg Ala
        35                  40                  45

Cys Phe Phe Ile Leu Gly Ala Gln Phe Ala Glu Thr Leu Cys Phe Phe
    50                  55                  60

Met Val Ser Lys Asn Leu Val Met Tyr Leu Thr Ser Ala Leu His Glu
65                  70                  75                  80

Ser Asn Ile Asp Ala Ala Gln Ser Val Ser Ile Trp Ile Gly Thr Ser
            85                  90                  95

Phe Phe Thr Pro Leu Ile Gly Ala Phe Leu Ala Asp Thr Tyr Trp Gly
            100                 105                 110

Arg Tyr Trp Thr Thr Val Ile Ser Leu Phe Ile Ile Ile Gly Met
        115                 120                 125

Leu Ile Val Thr Val Ser Ser Pro Leu Phe Leu Asn Ser Ser Tyr
    130                 135                 140
```

```
Tyr Asn Trp Asn Ile Cys Arg Ala Thr Val Tyr Thr Gly Leu Tyr Leu
145                 150                 155                 160

Thr Ala Val Gly Ser Gly Cys Met Lys Pro Cys Ile Pro Ala Phe Gly
                165                 170                 175

Ala Asp Gln Phe Asp Ser Ala Asp Pro Val Glu Arg Leu Ala Lys Gly
            180                 185                 190

Ser Phe Phe Asn Trp Tyr Tyr Phe Ser Met Asn Val Gly Ser Leu Leu
        195                 200                 205

Ser Thr Thr Leu Leu Val Trp Val Val Ala Asn Ile Gly Trp Ser Val
    210                 215                 220

Gly Phe Ala Ile Pro Met Leu Leu Ser Gly Phe Gly Leu Ala Leu Phe
225                 230                 235                 240

Phe Ala Gly Arg Lys Val Tyr Arg Tyr Lys Lys Gln Gly Gly Ser Pro
                245                 250                 255

Leu Thr Arg Val Ser Gln Val Val Ala Ala Val Arg Asn His Arg
            260                 265                 270

Leu Lys Leu Pro Asp Asp Ser Leu Leu His Glu Val Ser Lys Val
        275                 280                 285

Thr Glu Asp Asp Tyr Arg Thr Gln Leu Thr Thr Gln Phe Arg Phe Phe
290                 295                 300

Asp Lys Ala Ala Ile Leu Ser Asp Glu Ile Ser Pro Ala Gln Trp Ser
305                 310                 315                 320

Pro Trp Arg Leu Cys Thr Val Ser Gln Val Glu Glu Leu Lys Ile Leu
                325                 330                 335

Leu Arg Met Phe Pro Val Trp Val Ser Met Val Val Phe Val Val
            340                 345                 350

Thr Ala Gln Ile Thr Ser Thr Leu Ile Glu Gln Gly Met Ala Met Asp
                355                 360                 365

Gly Arg Val Gly Pro Phe Thr Leu Pro Ala Ala Ser Ile Ala Thr Phe
    370                 375                 380

Asp Val Ile Ser Val Leu Val Trp Val Pro Val Tyr Asp Thr Val Leu
385                 390                 395                 400

Val Pro Leu Ala Arg Arg Val Thr Gly Lys Asp Arg Gly Ile Ser His
                405                 410                 415

Leu Gln Arg Ile Gly Val Gly Leu Ala Leu Ala Ala Val Ala Met Ala
            420                 425                 430

Tyr Ser Ala Val Val Glu Ala Arg Arg Leu Gly Thr Ala Pro Ala Pro
    435                 440                 445

Val Ser Ile Met Trp Gln Ala Pro Ser Tyr Leu Val Leu Gly Val Ala
    450                 455                 460

Glu Ala Phe Ser Val Ile Gly Met Met Glu Phe Phe Tyr Glu Gln Ser
465                 470                 475                 480

Pro Glu Ser Met Lys Ser Leu Cys Thr Ala Leu Gly Gln Leu Ala Ile
                485                 490                 495

Ala Val Ala Asn Tyr Leu Asn Ser Gly Val Leu Val Val Ala Ala
            500                 505                 510

Ala Thr Thr Arg Gly Gly Gly Ala Gly Trp Ile Pro Asp Asn Leu Asp
        515                 520                 525

Glu Gly His Leu Asp Tyr Phe Phe Trp Met Met Ala Val Val Ser Val
    530                 535                 540

Leu Asn Leu Leu His Phe Leu His Cys Ser Ile Arg Tyr Arg Ala Asn
545                 550                 555                 560
```

Asn Asn Thr Leu Ser Ser
          565

<210> SEQ ID NO 61
<211> LENGTH: 1752
<212> TYPE: DNA
<213> ORGANISM: Zea mays

<400> SEQUENCE: 61

| | |
|---|---:|
| atggatgccc aagacggcga tgagagaccg ctgatcatcc atcgcctgcc actactccag | 60 |
| gatgaaagta cttccgaatt cactagcgac gggacggttg atcttcgcaa tcagcctgct | 120 |
| cggaagcaga gaactgggaa gtggaaagca tgcttcttca tcttaggtgc cgagtttgct | 180 |
| gaatgtgtgg ccttcttcgc gatctcgaag aacctggtga cgtacctcac gggcgttctg | 240 |
| cacgagagca acgtggacgc cgcgacgact gtgtccacct ggatcgggac ctcgttcttc | 300 |
| acgccgctcg tcggcgcgtt cttggccgac acattctggg ggcgatactg gacgatactg | 360 |
| gccttcctct ccgtgtacgt cacggggatg acggtcctga ctgcttcagc tcttctcccg | 420 |
| ctgctcatgg gcgcgtccta cagccgtagc gcccaccgcc tcttcgcgta cctgggcctc | 480 |
| tacctcgccg ctctcggcac cggcggaatc aagccgtgcg tctgcgcgct cggtgccgac | 540 |
| cagttcgacg cgtctgaccc cgtggagcgg cgggccaagg gctccttctt caactggtac | 600 |
| tacttctcca tcaacatcgg ctccctgctg tccgcgacgg tggtcgtctg ggtgcaggac | 660 |
| aacgttgggt ggggagtcgg gttcgcgatc ccgaccctgc tcatgctgtc gggactcgtg | 720 |
| ctgttcgtcg ccggtaggaa ggtttacagg taccagagag tggggagggag ccctctgaca | 780 |
| agagcctcgc aggtggtggt tgctgctgtc aggaactacc gtttggtgct gcctgagcct | 840 |
| gacgacagct cggccctgct gcatcaggcg cctcccggaa cgacggaagg aaatgattcc | 900 |
| acgatgcagc atacgagtca attcaggttc cttgacaagg ctgccattgt agcgccatcc | 960 |
| tccggcgaga aggagcgac ggcaagccca tggcggctct gcacggtctc ccaggtcgag | 1020 |
| gagctgaaga cggtgctgcg gatgttcccc gtgtgggtgt cgatggtgct cttcttcgcg | 1080 |
| gccaccgcgc agatgtcgtc caccttcatc gagcaaggcg agaccatgga caaccgcgtg | 1140 |
| gggccgttca ccgtgccgcc ggcgtccctc tccaccttcg acgtcatcag cgtcatggtc | 1200 |
| tgcataccca tctacgacaa agcgctggtg ccgctggccc ggcgcgccac gggcaaggag | 1260 |
| cggggcctgt cgcagctgca gcggctgggc gtcggcctcg cgctgtccgt ggccggcatg | 1320 |
| gtgtacgcgg cgctgctcga ggccaggcgg ctgtcgctcg cccgcgcagc ggcggacggg | 1380 |
| cggccgccga tgtccatcat gtggcaggcg ccggcgttcg cggtgctcgg cgccggggag | 1440 |
| gtgttcgcga ccatcggcat cctcgagttc ttctacgacc agtcgcccga cggcatgaag | 1500 |
| agcctcggca cggcccttgc gcagctgccg tcgcggcag caactactt caactctgcc | 1560 |
| gtgctcgccg ccgtcgccgc cgtcaccacg cgcaacgggg aggcaggatg gatccccgac | 1620 |
| gacctggaca agggccacct cgactatttc ttctggttca tggctgttct cggcgtggtc | 1680 |
| aacctgctgc acttcctgca ttgctccgtc aggtacagag gcagcagcaa caacagcaca | 1740 |
| tactcttctt ga | 1752 |

<210> SEQ ID NO 62
<211> LENGTH: 583
<212> TYPE: PRT
<213> ORGANISM: Zea mays

<400> SEQUENCE: 62

```
Met Asp Ala Gln Asp Gly Asp Glu Arg Pro Leu Ile Ile His Arg Leu
1               5                   10                  15

Pro Leu Leu Gln Asp Glu Ser Thr Ser Glu Phe Thr Ser Asp Gly Thr
            20                  25                  30

Val Asp Leu Arg Asn Gln Pro Ala Arg Lys Gln Arg Thr Gly Lys Trp
        35                  40                  45

Lys Ala Cys Phe Phe Ile Leu Gly Ala Glu Phe Ala Glu Cys Val Ala
    50                  55                  60

Phe Phe Ala Ile Ser Lys Asn Leu Val Thr Tyr Leu Thr Gly Val Leu
65                  70                  75                  80

His Glu Ser Asn Val Asp Ala Ala Thr Thr Val Ser Thr Trp Ile Gly
            85                  90                  95

Thr Ser Phe Phe Thr Pro Leu Val Gly Ala Phe Leu Ala Asp Thr Phe
            100                 105                 110

Trp Gly Arg Tyr Trp Thr Ile Leu Ala Phe Leu Ser Val Tyr Val Thr
            115                 120                 125

Gly Met Thr Val Leu Thr Ala Ser Ala Leu Leu Pro Leu Leu Met Gly
            130                 135                 140

Ala Ser Tyr Ser Arg Ser Ala His Arg Leu Phe Ala Tyr Leu Gly Leu
145                 150                 155                 160

Tyr Leu Ala Ala Leu Gly Thr Gly Ile Lys Pro Cys Val Cys Ala
            165                 170                 175

Leu Gly Ala Asp Gln Phe Asp Ala Ser Asp Pro Val Glu Arg Arg Ala
            180                 185                 190

Lys Gly Ser Phe Phe Asn Trp Tyr Tyr Phe Ser Ile Asn Ile Gly Ser
            195                 200                 205

Leu Leu Ser Ala Thr Val Val Trp Val Gln Asp Asn Val Gly Trp
210                 215                 220

Gly Val Gly Phe Ala Ile Pro Thr Leu Leu Met Leu Ser Gly Leu Val
225                 230                 235                 240

Leu Phe Val Ala Gly Arg Lys Val Tyr Arg Tyr Gln Arg Val Gly Gly
            245                 250                 255

Ser Pro Leu Thr Arg Ala Ser Gln Val Val Val Ala Ala Val Arg Asn
            260                 265                 270

Tyr Arg Leu Val Leu Pro Glu Pro Asp Asp Ser Ser Ala Leu Leu His
            275                 280                 285

Gln Ala Pro Pro Gly Thr Thr Glu Gly Asn Asp Ser Thr Met Gln His
            290                 295                 300

Thr Ser Gln Phe Arg Phe Leu Asp Lys Ala Ala Ile Val Ala Pro Ser
305                 310                 315                 320

Ser Gly Glu Lys Gly Ala Thr Ala Ser Pro Trp Arg Leu Cys Thr Val
            325                 330                 335

Ser Gln Val Glu Glu Leu Lys Thr Val Leu Arg Met Phe Pro Val Trp
            340                 345                 350

Val Ser Met Val Leu Phe Ala Ala Thr Ala Gln Met Ser Ser Thr
            355                 360                 365

Phe Ile Glu Gln Gly Glu Thr Met Asp Asn Arg Val Gly Pro Phe Thr
            370                 375                 380

Val Pro Pro Ala Ser Leu Ser Thr Phe Asp Val Ile Ser Val Met Val
385                 390                 395                 400

Cys Ile Pro Ile Tyr Asp Lys Ala Leu Val Pro Leu Ala Arg Arg Ala
            405                 410                 415

Thr Gly Lys Glu Arg Gly Leu Ser Gln Leu Gln Arg Leu Gly Val Gly
```

-continued

```
                    420                 425                 430
Leu Ala Leu Ser Val Ala Gly Met Val Tyr Ala Ala Leu Leu Glu Ala
            435                 440                 445
Arg Arg Leu Ser Leu Ala Arg Ala Ala Ala Asp Gly Arg Pro Pro Met
        450                 455                 460
Ser Ile Met Trp Gln Ala Pro Ala Phe Ala Val Leu Gly Ala Gly Glu
465                 470                 475                 480
Val Phe Ala Thr Ile Gly Ile Leu Glu Phe Phe Tyr Asp Gln Ser Pro
                485                 490                 495
Asp Gly Met Lys Ser Leu Gly Thr Ala Leu Ala Gln Leu Ala Val Ala
            500                 505                 510
Ala Gly Asn Tyr Phe Asn Ser Ala Val Leu Ala Ala Val Ala Ala Val
        515                 520                 525
Thr Thr Arg Asn Gly Glu Ala Gly Trp Ile Pro Asp Asp Leu Asp Lys
    530                 535                 540
Gly His Leu Asp Tyr Phe Phe Trp Phe Met Ala Val Leu Gly Val Val
545                 550                 555                 560
Asn Leu Leu His Phe Leu His Cys Ser Val Arg Tyr Arg Gly Ser Ser
                565                 570                 575
Asn Asn Ser Thr Tyr Ser Ser
            580
```